United States Patent
Hirai et al.

(10) Patent No.: US 9,012,475 B2
(45) Date of Patent: Apr. 21, 2015

(54) METHOD FOR ENHANCING ANTI-TUMOR EFFECT OF A MICROTUBULE-TARGETING DRUG, AND A METHOD FOR TREATMENT OF TUMOR

(71) Applicant: Taiho Pharmaceutical Co., Ltd., Chiyoda-ku (JP)

(72) Inventors: Hiroshi Hirai, Tsukuba (JP); Hiroshi Sootome, Tsukuba (JP)

(73) Assignee: Taiho Pharmaceutical Co., Ltd., Chiyoda-ku (JP)

( * ) Notice: Subject to any disclaimer, the term of this patent is extended or adjusted under 35 U.S.C. 154(b) by 0 days.

(21) Appl. No.: 14/010,684

(22) Filed: Aug. 27, 2013

(65) Prior Publication Data
US 2015/0065479 A1 Mar. 5, 2015

(51) Int. Cl.
  A61K 31/445 (2006.01)
  A61K 31/335 (2006.01)
  A61K 47/22 (2006.01)
  A61K 31/337 (2006.01)
  A61K 31/415 (2006.01)

(52) U.S. Cl.
  CPC ............... *A61K 47/22* (2013.01); *A61K 31/337* (2013.01); *A61K 31/415* (2013.01)

(58) Field of Classification Search
  CPC ......................... A61K 31/337; A61K 31/415
  USPC ................................................. 514/315, 449
  See application file for complete search history.

(56) References Cited

FOREIGN PATENT DOCUMENTS

WO WO 2013/129443 A1 9/2013

OTHER PUBLICATIONS

Silvia Lapenna, et al., "Cell cycle kinases as therapeutic targets for cancer", Nature Reviews Drug Discovery, vol. 8, Jul. 2009, pp. 547-566.
Giannis Mountzios, et al, "Aurora kinases as targets for cancer therapy", Cancer Treatment Reviews, vol. 34, 2008, pp. 175-182.
Hiroshi Y. Yamada, et al., "Spindle checkpoint function and cellular sensitivity to antimitotic drugs", Mol Cancer Ther., vol. 5, 2006, pp. 2963-2969.
Shubha Anand, et al., "Aurora—A amplification overrides the mitotic spindle assembly checkpoint, inducing resistance to Taxol", Cancer Cell, vol. 3, Jan. 2003, pp. 51-62.
Tatsuo Hata, et al., "RNA Interference Targeting Aurora Kinase a Suppresses Tumor Growth and Enhances the Taxane Chemosensitivity in Human Pancreatic Cancer Cells" Cancer Research, vol. 65, 2005, pp. 2899-2905 with cover page.
Phillip Kaestner, et al., "Determinants for the efficiency of anticancer drugs targeting either Aurora—A or Aurora—B kinases in human colon carcinoma cells", Molecular Cancer Therapeutics, Jul. 2009, vol. 8, pp. 2046-2056 with cover page.
Toshiyasu Shimomura, et al., "MK-5108, a Highly Selective Aurora—A Kinase Inhibitor, Shows Antitumor Activity Alone and in Combination with Docetaxel", Molecular Cancer Therapeutics, Jan. 2010, vol. 9, pp. 157-166 with cover page.
"24th EOTRC-NCI-AACR Symposium on Molecular Targets and Cancer Therapeutics", European Journal of Cancer, AS-2104, a Highly potent and selective Aurora A inhibitor, enhanced antitumor activity of taxanes in vivo (252), Poster of Conference, vol. 48, Nov. 6-9, 2012, 2 pages with cover page.

*Primary Examiner* — Kevin E Weddington
(74) *Attorney, Agent, or Firm* — Oblon, McClelland, Maier & Neustadt, L.L.P.

(57) ABSTRACT

A method for treating a tumor by combining a piperidine compound of formula (I) or salt thereof and a microtubule-targeting drug, in which the microtubule-targeting drug is administered once per 7 days or more one cycle, and the piperidine compound is administered once or more per day for 4 days or more:

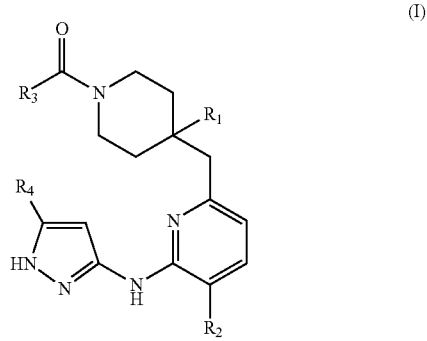

(I)

$R_1$ represents a carboxyl group, —C(=O)NR$_5$R$_6$, or an oxadiazolyl group optionally substituted with a $C_1$-$C_6$ alkyl group or trifluoromethyl group;
$R_2$ represents a halogen atom or $C_1$-$C_6$ alkoxy group;
$R_3$ represents a phenyl group optionally having 1 to 3 groups, selected from a halogen atom, and a $C_1$-$C_6$ alkyl, $C_1$-$C_6$ alkoxy, or trifluoromethyl group;
$R_4$ represents a hydrogen atom or $C_1$-$C_6$ alkyl group; and
$R_5$ and $R_6$, each represent a hydrogen atom, a $C_1$-$C_6$ alkyl or $C_3$-$C_6$ cycloalkyl group; or $R_5$ and $R_6$, together with a nitrogen atom, optionally form a 3 to 6-membered nitrogen-containing saturated heterocyclic group.

12 Claims, 3 Drawing Sheets

| (A) | Sequential treatment | | | | | | | Efficacy | |
|---|---|---|---|---|---|---|---|---|---|
| | | Day 1 | 2 | 3 | 4 | 5 | 10 | T/C (%) | CR |
| | Paclitaxel; 10mg/kg (i.v.) ⇑ | | | | | | Efficacy | 39 | 0/5 |
| | Compound 1; | 1 day | ⇑ | | | | | 11 | 0/5 |
| | 30 mg/kg (p.o.) | 4 days ⇑ | ⇑ | ⇑ | ⇑ | | | 3 | 2/5 |

| (B) | Concurrent treatment | | | | | | | Efficacy | |
|---|---|---|---|---|---|---|---|---|---|
| | | Day 1 | 2 | 3 | 4 | 5 | 10 | T/C (%) | CR |
| | Paclitaxel; 10mg/kg (i.v.) ⇑ | | | | | | Efficacy | 39 | 0 |
| | Compound 1; | 2 days ⇑ | ⇑ | | | | | 1 | 1/5 |
| | 30 mg/kg (p.o.) | 4 days ⇑ | ⇑ | ⇑ | ⇑ | | | 2 | 4/5 |

T/C defined as the relative size of treated and control tumors CR; complete response

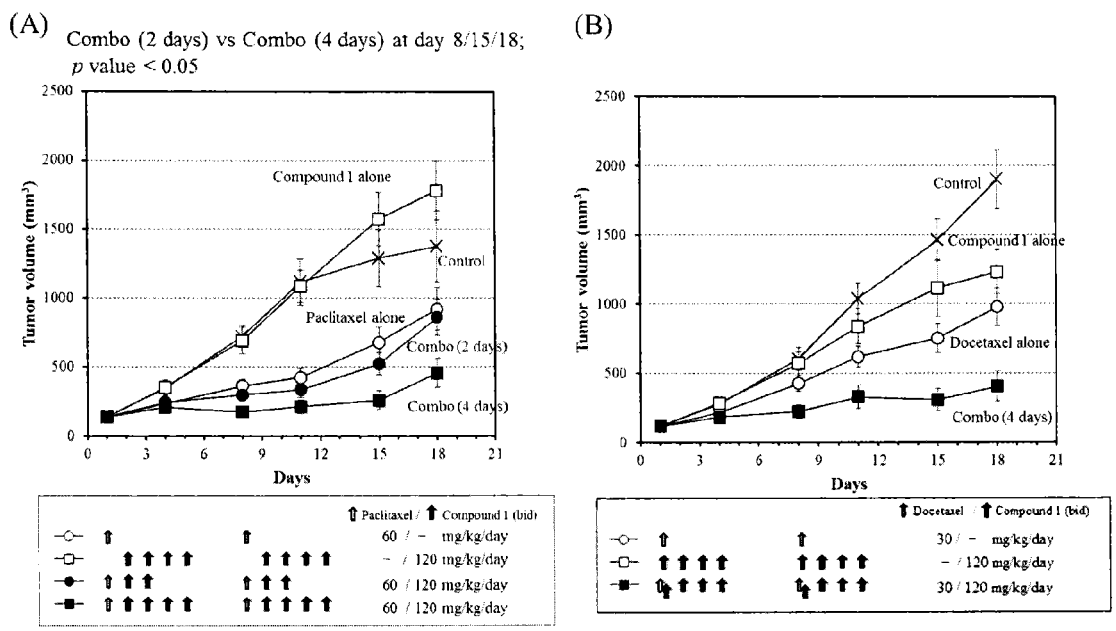

Fig. 2 (A) Antitumor efficacy of combination of paclitaxel and Compound 1 against H460 human lung carcinoma xenograft model.

Each plot and bar indicate the mean and the standard error of the means, respectively (n = 9-10).

Fig. 2 (B) Antitumor efficacy of combination of docetaxel and Compound 1 against H460 human lung carcinoma xenograft model.

Each plot and bar indicate the mean and the standard error of the means, respectively (n = 10).

Figure 3
(A)
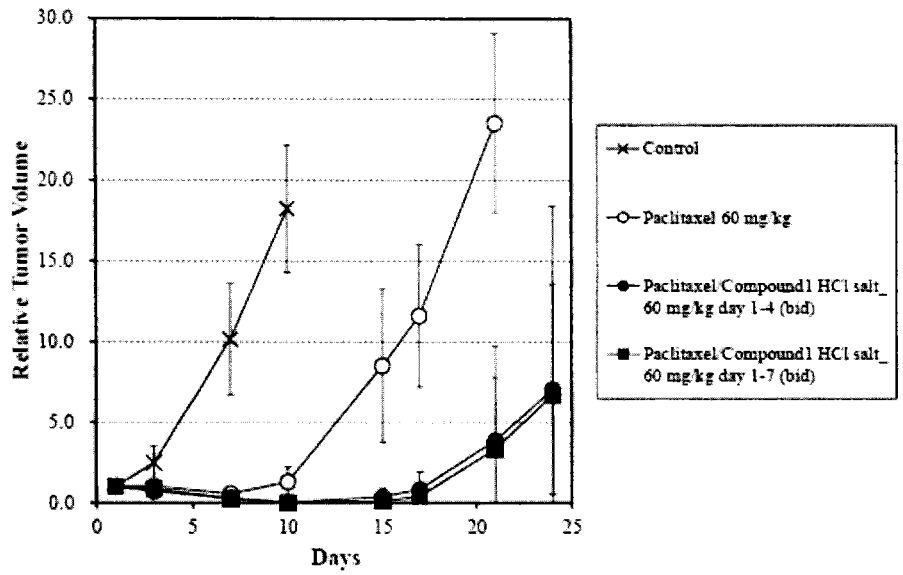
Fig. 3 (A) Antitumor efficacy of combination of Paclitaxel and the hydrochloride salt form of compound 1 against A2780 human ovarian carcinoma xenograft model.
(B)
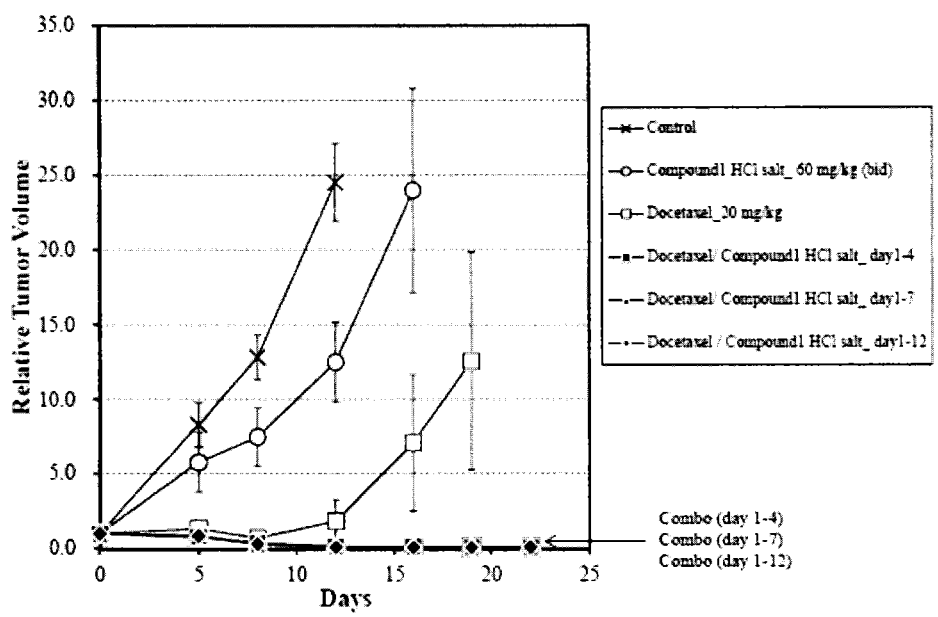
Fig. 3 (B) Antitumor efficacy of combination of Docetaxel and the hydrochloride salt form of compound 1 against A2780 human ovarian carcinoma xenograft model.

METHOD FOR ENHANCING ANTI-TUMOR EFFECT OF A MICROTUBULE-TARGETING DRUG, AND A METHOD FOR TREATMENT OF TUMOR

FIELD OF THE INVENTION

The present invention relates to a method for enhancing an antitumor effect of a microtubule-targeting drug by using an Aurora A selective inhibitor, and further to a method for treating a tumor by a combination of a microtubule-targeting drug and an Aurora A selective inhibitor.

BACKGROUND OF THE INVENTION

Aurora A is a serine/threonine kinase. It is reported that Aurora A is involved in e.g., formation and maturation of a centrosome, spindle kinetics and chromosome alignment in the mitotic phase (M phase) of the cell cycle and regulates a process of mitotic division (Non Patent Document 1). Up to present, it has been confirmed that Aurora A is excessively expressed and/or amplified in a wide variety of types of carcinomas (Non Patent Document 2). Furthermore, inhibition of Aurora A kinase in a tumor cell induces arrest of mitotic division and induction of apoptosis. Thus, Aurora A is an important target molecule for cancer treatment.

Microtubule-targeting drugs such as taxane antitumor agents and vinca alkaloids have been widely used as cancer chemotherapeutic agents. However, due to refractoriness and resistance to these agents, sufficient therapeutic effects are not sometimes obtained. Thus, it is expected that an agent capable of enhancing the antitumor effect of a taxane antitumor agent can more effectively treat cancer. In the cytotoxicity reaction of a taxane antitumor agent, it is required to activate a spindle assembly checkpoint in a cell cycle. In tumor cells reduced in this activity, sensitivity to a taxane antitumor agent decreases (Non Patent Document 3), in addition, a cell strain, in which Aurora A is excessively expressed, develops resistance to paclitaxel (Non Patent Document 4). Thus, it has been reported that an effect of paclitaxel or docetaxel is enhanced if Aurora A is inhibited (Non Patent Document 5).

In the meantime, Aurora B, which is a subtype of Aurora A, acts on the mitotic phase (M phase) of the cell cycle similarly to Aurora A. However, it has been reported that if Aurora B is inhibited, the activity of a spindle checkpoint is reduced (Non Patent Document 6). Thus, there is a possibility that inhibition of Aurora B may attenuate the effect of a taxane antitumor agent. From the descriptions above, it is expected that if an agent selectively inhibiting Aurora A kinase is used in combination with a taxane antitumor agent, its antitumor effect can be enhanced to produce a higher therapeutic effect.

Under the above circumstance, MK-5108 is reported as an Aurora A selective inhibitor (Non Patent Document 7). In this document, an antitumor effect is evaluated by administering MK-5108 and docetaxel to nude rats. To describe it more specifically, docetaxel is administered and then, 24 hours later, MK-5108 is orally administered twice per day over 2 days. Although enhancement of an antitumor effect is confirmed, its therapeutic effect is not sufficient.

CITATION LISTS

Non Patent Document

Non Patent Document 1 Nat. Rev. Drug Discov., 8, p 547-566 (2009)

Non Patent Document 2 Cancer Treat. Rev., 34, p 175-182 (2008)

Non Patent Document 3 Mol. Cancer Ther., 5, p 2963-2969 (2006)

Non Patent Document 4 Cancer Cell, 3, p 51-62 (2003)

Non Patent Document 5 Cancer Res., 65, p 2899-2905 (2005)

Non Patent Document 6 Mol, Cancer Ther., 8, p 2046-2056 (2009)

Non Patent Document 7 Mol. Cancer. Ther., 9, p 157-166 (2010)

SUMMARY OF THE INVENTION

Problems to be Solved by the Invention

However, a method for treating a tumor significantly enhancing the antitumor effect of a microtubule-targeting drug represented by a taxane antitumor agent to produce an excellent therapeutic effect has never been known.

Thus, an object of the present invention is to provide an effective method for treating a tumor by using an orally available Aurora A selective inhibitor in combination with a microtubule-targeting drug (in particular, a taxane antitumor agent).

Means for Solving the Problems

Then, the present inventors found that a piperidine compound represented by the following general formula (I) or a salt thereof has a strong Aurora A selective inhibitory effect, and that if a microtubule-targeting drug and the piperidine compound or a salt thereof are administered according to a predetermined schedule, a particularly excellent antitumor effect can be obtained. Based on the findings, the present invention was accomplished.

More specifically, the present invention provides the following [1] and [2].

[1] A method for enhancing an antitumor effect of a microtubule-targeting drug by administering a piperidine compound represented by general formula (I) or a salt thereof, wherein the following administration schedule thereof is performed:

the microtubule-targeting drug is administered once per 7 days or more as one cycle, and the piperidine compound or a salt thereof is administered once or more per day for 4 days or more:

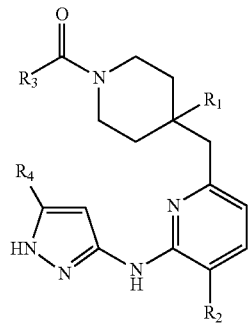

(I)

wherein $R_1$ represents a carboxyl group, —C(=O)NR$_5$R$_6$, or an oxadiazolyl group which is optionally substituted with a $C_1$-$C_6$ alkyl group or a trifluoromethyl group;

$R_2$ represents a halogen atom or a $C_1$-$C_6$ alkoxy group;

$R_3$ represents a phenyl group which is optionally substituted with 1 to 3 groups, which are the same or different, selected from a halogen atom, a $C_1$-$C_6$ alkyl group, a $C_1$-$C_6$ alkoxy group and a trifluoromethyl group, as a substituent(s);

$R_4$ represents a hydrogen atom or a $C_1$-$C_6$ alkyl group; and $R_5$ and $R_6$, which are the same or different, each represent a hydrogen atom, a $C_1$-$C_6$ alkyl group or a $C_3$-$C_6$ cycloalkyl group; or $R_5$ and $R_6$, together with a nitrogen atom to which they are attached, optionally form a 3 to 6-membered nitrogen-containing saturated heterocyclic group.

[2] A method for treating a tumor by administering a piperidine compound represented by general formula (I) or a salt thereof in combination with a microtubule-targeting drug, wherein the following administration schedule thereof is performed:

the microtubule-targeting drug is administered once per 7 days or more as one cycle, and the piperidine compound or a salt thereof is administered once or more per day for 4 days or more.

Advantageous Effects of the Invention

According to the administration schedule of the present invention, an excellent antitumor effect can be obtained by synergistic action between a microtubule-targeting drug and a piperidine compound as mentioned above or a salt thereof and an effect of reducing the volume of a target cancer is significant. Furthermore, according to the administration schedule of the present invention, a side effect of a microtubule-targeting drug can be suppressed to a minimum. Moreover, even to a cancer, which has developed resistance to the microtubule-targeting drug administered, if the piperidine compound or a salt thereof is administered in combination, continuous administration of the microtubule-targeting drug can be expected.

BRIEF DESCRIPTION OF THE DRAWINGS

FIG. 1 shows a treatment schedule (sequential administration (A), concurrent administration (B)) of paclitaxel and an Aurora A selective inhibitor (Compound 1) and its efficacy.

FIG. 2 shows a treatment schedule (sequential administration (A), concurrent administration (B)) of paclitaxel (A) or docetaxel (B) and an Aurora A selective inhibitor (Compound 1) and its efficacy.

FIG. 3 shows a treatment schedule (concurrent administration (both (A) and (B))) of paclitaxel (A) or docetaxel (B) and an Aurora A selective inhibitor (Compound 1) and its efficacy.

EMBODIMENTS FOR CARRYING OUT THE INVENTION

In a compound (hereinafter, sometimes referred to as "the compound of the invention") used in the present invention and represented by general formula (I), the type of $R_2$ is important in view of oral absorption property and an effect of enhancing an antitumor effect of a microtubule-targeting drug. The compound of the invention is characterized in that $R_2$ is a halogen atom or a $C_1$-$C_6$ alkoxy group.

In general formula (I), $R_1$ represents a carboxyl group or —C(=O)NR$_5$R$_6$. Herein, $R_5$ and $R_6$, which are the same or different, each represent a hydrogen atom, a $C_1$-$C_6$ alkyl group or a $C_3$-$C_6$ cycloalkyl group. Alternatively, $R_5$ and $R_6$, together with a nitrogen atom to which they are attached, optionally form an azetidinyl group, a pyrrolidinyl group or an isoxazolidinyl group. $R_1$ is preferably a carboxyl group or an oxadiazolyl group which optionally has a methyl group or a trifluoromethyl group.

In general formula (I), $R_2$ is preferably a fluorine atom, a chlorine atom or a $C_1$-$C_4$ alkoxy group and further preferably a fluorine atom, a chlorine atom or a methoxy group.

In general formula (I), $R_3$ is preferably a phenyl group. $R_3$ optionally has 1 to 3 substituents, which are the same or different, selected from a halogen atom, a $C_1$-$C_4$ alkyl group, a $C_1$-$C_4$ alkoxy group and a trifluoromethyl group. The substituent(s) each preferably has 1 or 2 groups, which are the same or different, selected from a fluorine atom, a chlorine atom, a methyl group, a methoxy group and a trifluoromethyl group.

In general formula (I), $R_4$ is preferably a hydrogen atom or a methyl group.

In the compound of the invention, it is preferable that $R_1$ represents a carboxyl group, —C(=O)NR$_5$R$_6$ (wherein $R_5$ and $R_6$, which are the same or different, each represent a hydrogen atom, a $C_1$-$C_4$ alkyl group or a $C_3$-$C_6$ cycloalkyl group, or alternatively $R_5$ and $R_6$, together with a nitrogen atom to which they are attached, optionally form an azetidinyl group, a pyrrolidinyl group or an isoxazolidinyl group), or an oxadiazolyl group which optionally has a $C_1$-$C_4$ alkyl group or a trifluoromethyl group as a substituent; $R_2$ represents a fluorine atom, a chlorine atom or a $C_1$-$C_4$ alkoxy group; $R_3$ represents a phenyl group which optionally has 1 or 2 groups, which are the same or different, selected from a halogen atom, a $C_1$-$C_4$ alkyl group, a $C_1$-$C_4$ alkoxy group and a trifluoromethyl group, as a substituent(s); and $R_4$ represents a hydrogen atom or a $C_1$-$C_4$ alkyl group.

Furthermore, as the compound of the invention, a compound represented by general formula (I) wherein $R_1$ represents a carboxyl group, —C(=O)NR$_5$R$_6$ (wherein $R_5$ and $R_6$, which are the same or different, each represent a hydrogen atom, a methyl group, a cyclopropyl group or a cyclobutyl group, or alternatively $R_5$ and $R_6$, together with a nitrogen atom to which they are attached, optionally form an azetidinyl group, a pyrrolidinyl group or an isoxazolidinyl group), or an oxadiazolyl group which optionally has a methyl group or a trifluoromethyl group as a substituent; $R_2$ represents a fluorine atom, a chlorine atom or a methoxy group; $R_3$ represents a phenyl group which optionally has 1 or 2 groups, which are the same or different, selected from a fluorine atom, a chlorine atom, a methyl group, a methoxy group and a trifluoromethyl group, as a substituent(s); and $R_4$ represents a hydrogen atom or a methyl group, is preferable.

Furthermore, a compound wherein $R_1$ represents a carboxyl group, —C(=O)NR$_5$R$_6$ (wherein $R_5$ and $R_6$, which are the same or different, each represent a hydrogen atom or a methyl group, or alternatively $R_5$ and $R_6$, together with a nitrogen atom to which they are attached, optionally form an isoxazolidinyl group), or a 1,2,4-oxadiazolyl group or a 1,3,4-oxadiazolyl group which optionally has a methyl group as a substituent; $R_2$ represents a fluorine atom, a chlorine atom or a methoxy group; $R_3$ represents a phenyl group, which has 1 or 2 groups, which are the same or different, selected from a fluorine atom, a chlorine atom, a methyl group, a methoxy group and a trifluoromethyl group, as a substituent(s); and $R_4$ represents a hydrogen atom or a methyl group, is more preferable.

Moreover, a compound wherein $R_1$ represents a carboxyl group or a 1,2,4-oxadiazolyl group which optionally has a methyl group as a substituent; $R_2$ represents a fluorine atom; $R_3$ represents a phenyl group having 1 or 2 groups, which are the same or different, selected from a fluorine atom and a chlorine atom as a substituent(s); and $R_4$ represents a methyl group is particularly preferable.

Specific examples of the compound of the invention to be preferably used in a method for enhancing an antitumor effect and a method for treating a tumor according to the present invention include:

1-(2,3-dichlorobenzoyl)-4-((5-fluoro-6-(5-methyl-1H-pyrazol-3-ylamino)pyridin-2-yl)methyl)piperidine-4-carboxylic acid (compound 1)

1-(2-fluoro-3-trifluoromethylbenzoyl)-4-((5-fluoro-6-(5-methyl-1H-pyrazol-3-ylamino)pyridin-2-yl)methyl)piperidine-4-carboxylic acid (compound 2)

1-(3-chloro-2-fluorobenzoyl)-4-((5-fluoro-6-(1H-pyrazol-3-ylamino)pyridin-2-yl)methyl)piperidine-4-carboxylic acid (compound 10)

1-(3-chloro-2-fluorobenzoyl)-4-((5-methoxy-6-(5-methyl-1H-pyrazol-3-ylamino)pyridin-2-yl)methyl)piperidine-4-carboxylic acid (compound 11)

1-(3-chloro-2-fluorobenzoyl)-4-((5-chloro-6-(5-methyl-1H-pyrazol-3-ylamino)pyridin-2-yl)methyl)piperidine-4-carboxylic acid (compound 12)

1-(3-chloro-2-fluorobenzoyl)-4-((5-fluoro-6-(5-methyl-1H-pyrazol-3-ylamino)pyridin-2-yl)methyl)piperidine-4-carboxylic acid (compound 13)

1-(3-chloro-2-fluorobenzoyl)-4-((5-fluoro-6-(5-methyl-1H-pyrazol-3-ylamino)pyridin-2-yl)methyl)-N-methylpiperidine-4-carboxamide (compound 14)

1-(3-chloro-2-fluorobenzoyl)-4-((5-fluoro-6-(5-methyl-1H-pyrazol-3-ylamino)pyridin-2-yl)methyl)-N,N-dimethylpiperidine-4-carboxamide (compound 16)

azetidin-1-yl(1-(3-chloro-2-fluorobenzoyl)-4-((5-fluoro-6-(5-methyl-1H-pyrazol-3-ylamino)pyridin-2-yl)methyl)piperidine-4-yl)methanone (compound 19)

(1-(3-chloro-2-fluorobenzoyl)-4-((5-fluoro-6-(5-methyl-1H-pyrazol-3-ylamino)pyridin-2-yl)methyl)piperidine-4-yl)(isoxazolidin-2-yl)methanone (compound 21)

(3-chloro-2-fluorophenyl)(4-((5-fluoro-6-(5-methyl-1H-pyrazol-3-ylamino)pyridin-2-yl)methyl)-4-(5-methyl-1,2,4-oxadiazol-3-yl)piperidine-1-yl)methanone (compound 22)

(2,3-dichlorophenyl)(4-((5-fluoro-6-(5-methyl-1H-pyrazol-3-ylamino)pyridin-2-yl)methyl)-4-(5-methyl-1,2,4-oxadiazol-3-yl)piperidine-1-yl)methanone (compound 23)

(3-chloro-2-fluorophenyl)(4-((5-fluoro-6-(5-methyl-1H-pyrazol-3-ylamino)pyridin-2-yl)methyl)-4-(1,2,4-oxadiazol-3-yl)piperidine-1-yl)methanone (compound 24)

(3-chloro-2-fluorophenyl)(4-((5-fluoro-6-(5-methyl-1H-pyrazol-3-ylamino)pyridin-2-yl)methyl)-4-(5-methyl-1,3,4-oxadiazol-2-yl)piperidine-1-yl)methanone (compound 28)

(3-chloro-2-fluorophenyl)(4-((5-fluoro-6-(5-methyl-1H-pyrazol-3-ylamino)pyridin-2-yl)methyl)-4-(3-methyl-1,2,4-oxadiazol-5-yl)piperidine-1-yl)methanone (compound 29)

Among these compounds, Compound 1 or a salt thereof is particularly preferable.

A typical method for producing a compound (I) is hereinafter described. For example, the compound (I) can be produced by the process shown below or a method described in Examples.

Among the compounds (I), a compound (I-1) wherein $R_1$ represents a carboxyl group, can be produced by Process 1 shown below.

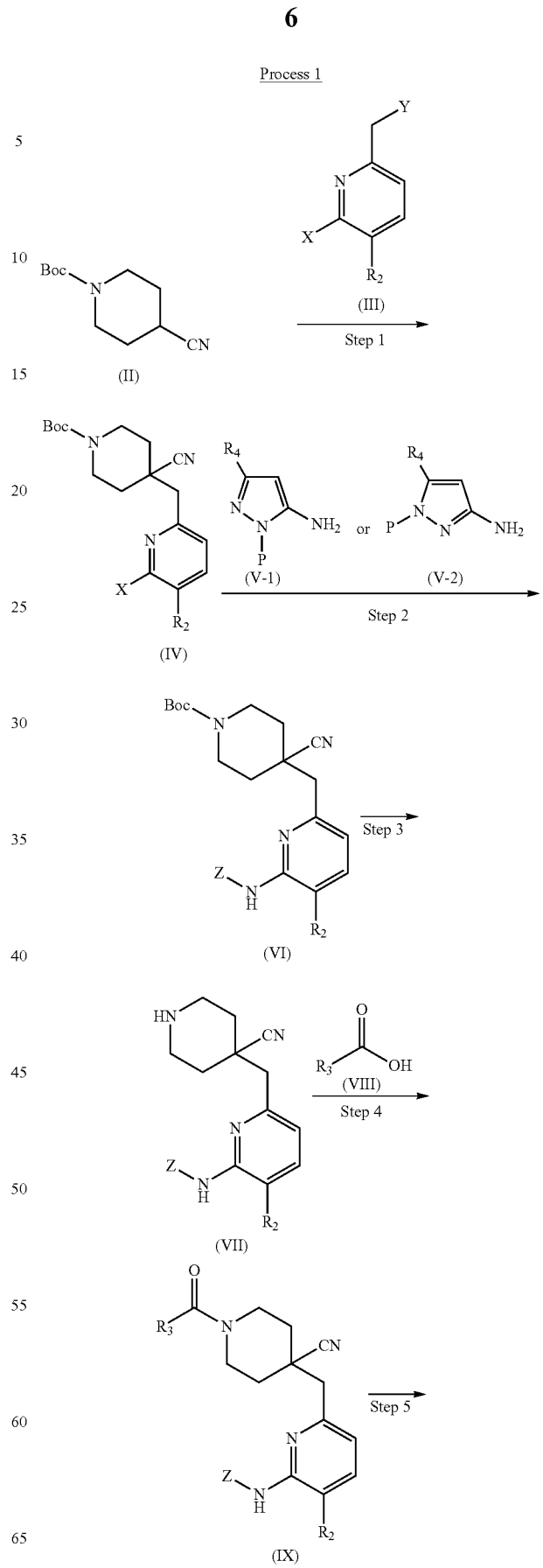

Process 1

-continued

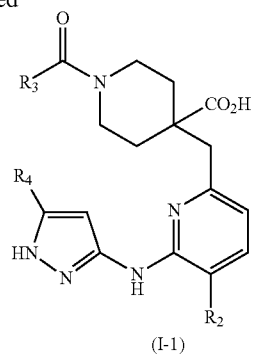

(In the formula, X and Y each represent a leaving group; P represents a hydrogen atom or a protecting group; and Z represents general formula (a) or (b)

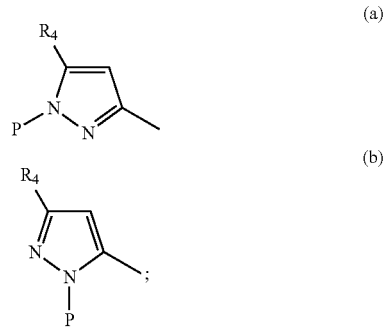

$R_2$, $R_3$ and $R_4$ are the same as previously defined.)

In Process 1, the leaving group represented by X or Y is a halogen atom and preferably a bromine atom. P represents a protecting group such as a tert-butyl group, a methoxymethyl group, a [(2-trimethylsilyl)ethoxy]methyl group and a benzyl group and preferably a tert-butyl group.

(Step 1)

This step relates to a method of producing a compound (IV) by reacting a compound (II) with a base and binding it to a compound (III). Examples of the compound (III) used in this step include 6-bromo-2-bromomethyl-5-fluoropyridine, 6-bromo-2-chloromethyl-5-fluoropyridine, 2-bromomethyl-6-chloro-5-fluoropyridine, 2-bromomethyl-5,6-dichloropyridine and 6-bromo-2-bromomethyl-5-methoxypyridine. 6-Bromo-2-bromomethyl-5-fluoropyridine is preferable. The compound (III) is commercially available or may be easily produced with reference to documents.

In this step, the amount of compound (III) relative to one equivalent of the compound (II) is 0.1 to 10 equivalents and preferably 0.8 to 2 equivalents. The reaction temperature is −90 to 100° C. and preferably −78 to 0° C. The reaction time is 0.1 to 100 hours and preferably 0.5 to 10 hours. Examples of the base include lithium diisopropylamide and lithium hexamethyldisilazide. The base may be used in an amount of 0.5 to 10 equivalents and preferably 1 to 1.5 equivalents. Examples of the solvent used in this step include tetrahydrofuran, 2-methyl tetrahydrofuran, diethyl ether, 1,2-dimethoxyethane and toluene. The solvent is not limited as long as it does not disturb the reaction. These solvents may be used alone or as a mixture.

(Step 2)

This step relates to a method of producing a compound (VI) by binding between a compound (IV) and a compound (V). Examples of the compound (V) (compound (V-1) or compound (V-2)) used in this step include 1-tert-butyl-3-methyl-1H-pyrazole-5-amine, 1-tert-butyl-1H-pyrazole-5-amine, 1-{[2-(trimethylsilyl)ethoxy]methyl}-1H-pyrazole-3-amine and 5-methyl-1-{[2-(trimethylsilyl)ethoxy]methyl}-1H-pyrazole-3-amine. The compound (V) is commercially available or may be produced by a known method.

The amount of compound (V) used in this step relative to one equivalent of the compound (IV) is 0.5 to 10 equivalents and preferably 0.8 to 2 equivalents. Examples of the catalyst which may be used include metal catalysts such as tris-benzylidene acetone dipalladium and palladium acetate. The catalyst may be used in an amount of 0.001 to 5 equivalents relative to one equivalent of the compound (IV) and preferably 0.005 to 0.1 equivalents. Examples of the ligand of the metal catalyst include 4,5-bis(diphenylphosphino)-9,9-dimethylxanthene, 2,2'-bis(diphenylphosphino)-1,1'-binaphthyl. The ligand may be used in an amount of 0.001 to 5 equivalents relative to one equivalent of the compound (IV) and preferably 0.005 to 0.2 equivalents. The reaction temperature is 0 to 200° C. and preferably room temperature to 130° C. The reaction time is 0.1 to 100 hours and preferably 0.5 to 20 hours. Examples of the base include inorganic bases such as potassium phosphate, sodium carbonate, potassium carbonate, cesium carbonate and sodium tert-butoxide and organic amines such as trimethylamine, diisopropylethylamine and pyridine. These bases each may be used in an amount of 0.5 to 10 equivalents and preferably 1 to 3 equivalents. Examples of the solvent used in the reaction include toluene, tetrahydrofuran, dioxane, N,N-dimethylformamide, N,N-dimethylacetamide, N-methylpyrrolidin-2-one, tert-butanol and tert-amyl alcohol. The solvent is not limited as long as it does not disturb the reaction. These solvents may be used alone or as a mixture.

(Step 3)

This step relates to a method of producing a compound (VII) by removing tert-butoxycarbonyl group serving as a protecting group of a compound (VI) in the presence of an acid. This step may be carried out with reference to a method described in the document (Protective Groups in Organic Synthesis, written by T. W. Greene, John Wiley & Sons Inc. (1981)). As the acid, e.g., trifluoroacetic acid, hydrochloric acid, sulfuric acid, methanesulfonic acid and toluenesulfonic acid may be used. The equivalent of the acid is 0.1 to 100 and preferably 1 to 10 equivalents. The reaction temperature is 0 to 200° C. and preferably room temperature to 100° C. The reaction time is 0.1 to 100 hours and preferably 0.5 to 20 hours. Examples of the solvent used in this reaction include chloroform, acetonitrile, toluene, tetrahydrofuran, dioxane, water and acetic acid. The solvent is not limited as long as it does not disturb the reaction. The solvent may be used alone or as a mixture.

(Step 4)

This step relates to a reaction for obtaining a compound (IX) by condensation between a compound (VII) and a compound (VIII). Examples of the compound (VIII) used in this step include 2-fluoro-3-chlorobenzoic acid and 2,3-dichlorobenzoic acid. The compound (VIII) is commercially available or may be produced by a known method. In this step, the condensing agent is one generally used and the compound (IX) can be obtained according to a known method. Examples of the condensing agent include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenyphosphoryl azide (DPPA), (benzotriazol-1- yl-oxy)trisdimethylaminophosphonium hexafluorophosphate (BOP), (benzotriazol-1-yl-oxy)tripyrrolidinophosphonium hexafluorophosphate (PyBOP), (7-azabenzotriazol-1-yloxy)trispyrrolidinophosphonium phosphate (PyAOP), bromotrispyrrolidinophosphonium hexafluorophosphate (BroP), chlorotris(pyrrolidin-1-yl)phosphonium hexafluorophosphate (PyCroP), 3-(diethoxyphosphoryloxy)-1,2,3-benzotriazin-4(3H)-one (DEPBT), O-(benzotriazol-1-yl)-N,N,N',N'-tetramethyluronium hexafluorophosphate (HATU) and 4-(4,6-dimethoxy-1,3,5-triazin-2-yl)-4-methylmorpholine hydrochloride (DMTMM). Examples of additives for the condensation include 1-hydroxybenzotriazole (HOBt), 1-hydroxy-7-azabenzotriazole (HOAt) and N-hydroxysuccinimide (HOSu). The additives may be used in an amount of 0.1 to 100 equivalents based on the condensing agent and preferably 1 to 10 equivalents. A base may be used as needed. Examples of the base include trimethylamine, triethylamine, tripropylamine, diisopropylethylamine, N-methylmorpholine, pyridine, 4-(N,N-dimethylamino)pyridine, lutidine and collidine. The base may be used in an amount of 0.1 to 100 equivalents and preferably 1 to 10 equivalents. Examples of the solvent include water, methanol, ethanol, 2-propanol, tetrahydrofuran, 1,4-dioxane, toluene, methylene chloride, chloroform, acetonitrile, N,N-dimethylformamide, N,N,-dimethylacetamide and dimethylsulfoxide. The reaction temperature is −30 to 200° C. and preferably 0 to 50° C. The reaction time is 0.1 to 100 hours and preferably 0.5 to 24 hours.

(Step 5)

This step relates to a method of producing a compound (I-1) by hydrolyzing the cyano group of a compound (IX) and removing a protecting group (P) of substituent Z under acidic conditions. Examples of the acid include hydrochloric acid, sulfuric acid, methanesulfonic acid, toluenesulfonic acid and trifluoroacetic acid. The acid may be used in an amount of 0.1 to 100 equivalents and preferably 1 to 10 equivalents. The reaction temperature is room temperature to 200° C. and preferably 60 to 130° C. The reaction time is 0.1 to 100 hours and preferably 0.5 to 20 hours. Examples of the solvent used in this reaction include dioxane, water, acetic acid, toluene, tetrahydrofuran and 2-propanol. The solvent is not particularly limited as long as it does not disturb the reaction. These solvents may be used alone or as a mixture.

Of the compounds represented by general formula (I), a compound (I-2) wherein $R_1$ represents —C(=O)$NR_5R_6$ can be produced, for example, by Process 2 shown below.

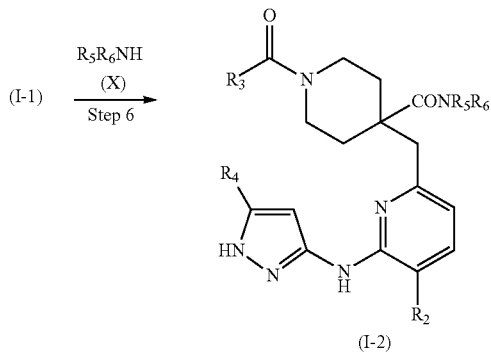

Process 2

(In the formula, $R_2$, $R_3$, $R_4$, $R_5$ and $R_6$ are the same as previously defined.)

(Step 6)

This step relates to a method of producing a compound (I-2) by a dehydration condensation reaction between the compound (I-1) obtained in Process 1 and a compound (X). Examples of the compound (X) used in this step include amines such as methylamine, dimethylamine, ammonium chloride, cyclopropylamine and pyrrolidine and salts thereof. The compound (X) is commercially available or can be produced according to a known method. In this step, a compound (I-2) can be obtained according to a known method using a condensing agent generally used. Examples of the condensing agent include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenylphosphorylazide (DPPA), (benzotriazol-1-yl-oxy)trisdimethylaminophosphonium hexafluorophosphate (BOP), (benzotriazol-1-yl-oxy)tripyrrolidinophosphonium hexafluorophosphate (PyBOP), (7-azabenzotriazol-1-yloxy)trispyrrolidinophosphonium phosphate (PyAOP), bromotrispyrrolidinophosphonium hexafluorophosphate (BroP), chlorotris(pyrrolidin-1-yl)phosphonium hexafluorophosphate (PyCroP), 3-(diethoxyphosphoryloxy)-1,2,3-benzotriazin-4(3H)-one (DEPBT), O-(benzotriazol-1-yl)-N,N,N',N'-tetramethyluronium hexafluorophosphate (HATU) and 4-(4,6-dimethoxy-1,3,5-triazin-2-yl)-4-methylmorphorine hydrochloride (DMTMM). Examples of the additives include 1-hydroxybenzotriazole (HOBt), 1-hydroxy-7-azabenzotriazole (HOAt) and N-hydroxysuccinimide (HOSu). These additives may be used in an amount of 0.1 to 100 equivalents and preferably 1 to 10 equivalents. If necessary, a base such as trimethylamine, triethylamine, tripropylamine, diisopropylethylamine, N-methylmorpholine, pyridine, 4-(N,N-dimethylamino)pyridine, lutidine and collidine may be used. The base may be used in an amount of 0.1 to 100 equivalents and preferably 1 to 10 equivalents. As the solvent, water, methanol, ethanol, 2-propanol, tetrahydrofuran, 1,4-dioxane, toluene, methylene chloride, chloroform, acetonitrile, N,N-dimethylformamide, N,N,-dimethylacetamide and dimethylsulfoxide may be used. The reaction temperature is −30 to 200° C. and preferably 0 to 50° C. The reaction time is 0.1 to 100 hours and preferably 0.5 to 24 hours.

Of the compounds represented by general formula (I), a compound (I-3), i.e., in which $R_1$ is 1,2,4-oxadiazole substituted with $R_7$, can be produced, for example, by Process 3 shown below.

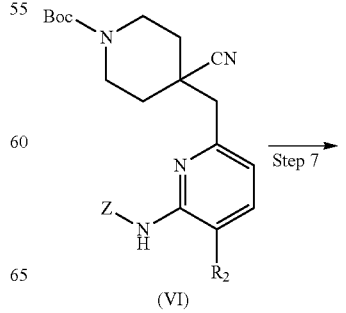

Process 3

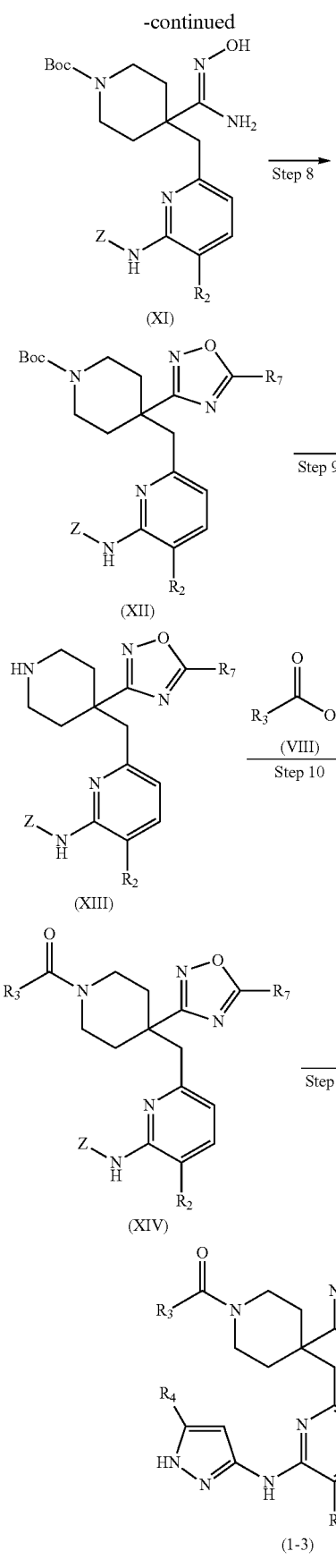

(In the formula, $R_7$ represents a $C_1$-$C_6$ alkyl group or a trifluoromethyl group; and $R_2$, $R_3$, $R_4$, $R_5$, $R_6$ and Z are the same as previously defined.)

(Step 7)

This step relates to a method of producing a compound (XI) by converting the cyano group of the compound (VI), which is obtained by Process 1 as an intermediate, into an amidoxime. The reaction employed in this step may be carried out according to a method described in, for example, any one of International Publication No. WO2005/026123, International Publication No. WO2008/117175 and International Publication No. WO2008/156721, or an equivalent method thereto. For example, conversion can be made by reacting the compound (VI) with a hydroxylamine in an alcohol solvent such as ethanol and 2-propanol. If necessary, a base is optionally used. Examples of the base include organic amines such as triethylamine, diisopropylethylamine, N-methylmorpholine and pyridine; and inorganic salts such as sodium hydrogen carbonate, sodium carbonate, potassium carbonate, cesium carbonate, sodium methoxide, sodium ethoxide and potassium tert-butoxide. Hydroxylamine may be used in an amount of 1 to 100 equivalents and preferably 1 to 10 equivalents. The reaction temperature is room temperature to 150° C. and preferably 50 to 100° C. The reaction time is 0.1 to 100 hours and preferably 0.5 to 20 hours.

(Step 8)

This step relates to a method of producing a compound (XII) by converting an amidoxime group of the compound (XI) into a 1,2,4-oxadiazol ring. The reaction employed in this step, may be carried out according to a method described in, for example, any one of International Publication No. WO2005/026123, International Publication No. WO2008/117175, and International Publication No. WO2008/156721 or an equivalent method thereto. For example, conversion can be made by reacting the compound (XI) with e.g., acetic anhydride, acetyl chloride, triethyl orthoformate or triethyl orthoacetate in a solvent such as toluene, chloroform, acetic acid, N,N-dimethylformamide, N-methylpyrrolidin-2-one and pyridine. If necessary, a base may be used. Examples of the base include triethylamine, diisopropylethylamine, N-methylmorpholine and pyridine. The reaction temperature is room temperature to 150° C. and preferably 50 to 100° C. The reaction time is 0.1 to 100 hours and preferably 0.5 to 20 hours.

(Step 9)

This step relates to a method of producing a compound (XIII) by removing a tert-butoxycarbonyl group of the compound (XII) serving as a protecting group in the presence of an acid. This step may be carried out in the same manner as in the Step 3 or an equivalent method thereto.

(Step 10)

his step relates to a method of producing a compound (XIV) by a dehydration condensation reaction between a compound (XIII) and a compound (VIII). This step may be carried out in the same manner as in the Step 4 or an equivalent method thereto.

(Step 11)

This step relates to a method of producing a compound (I-3) by removing a protecting group (P) of substituent Z of the compound (XIV) in the presence of an acid. This step may be carried out in the same manner as in the Step 5 or an equivalent method thereto.

Of the compounds represented by general formula (I), a compound (I-4), i.e., in which $R_1$ is 1,3,4-oxadiazole substituted with $R_7$, obtained by substituting $R_1$ with $R_7$, can be produced, for example, by Process 4 shown below.

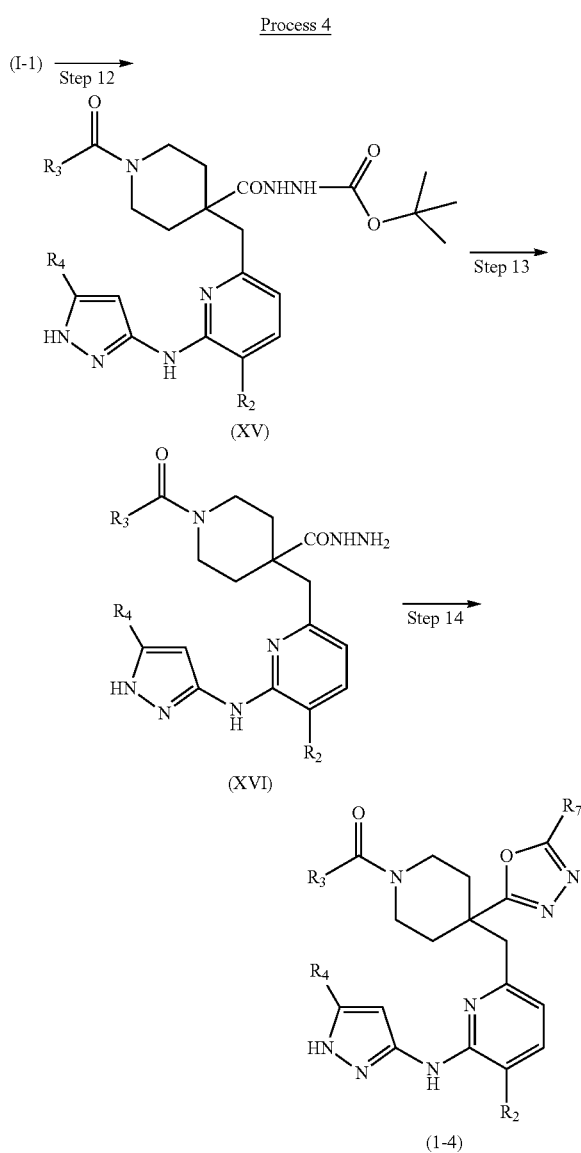

Process 4

(In the formula, $R_7$ represents a $C_1$-$C_6$ alkyl group or a trifluoromethyl group; and $R_2$, $R_3$ and $R_4$ are the same as previously defined.)

(Step 12)

This step relates to a method of producing a compound (XV) by a dehydration condensation reaction between the compound (I-1) obtained in Process 1 and tert-butoxycarbonylhydrazide. This step may be carried out in the same manner as in the Step 4 or an equivalent method thereto.

(Step 13)

This step relates to a method of producing a compound (XVI) by removing a tert-butoxycarbonyl group of the compound (XV) serving as a protecting group in the presence of an acid. This step may be carried out in the same manner as in the Step 3 or an equivalent method thereto.

(Step 14)

This step relates to a method of producing a compound (I-4) by converting the acyl hydrazide group of the compound (XVI) into a 1,3,4-oxadiazole ring. This step may be carried out in the same manner as in the Step 8 or an equivalent method thereto.

The compound of the invention obtained as described above is isolated and purified by a known separation/purification means such as concentration, concentration under vacuum, crystallization, solvent extraction, reprecipitation and chromatography or may be subjected to a next step without being isolated and purified.

If the compound of the invention has an isomer such as an enantiomer, a stereoisomer, a regioisomer and a rotamer, a mixture of any one of isomers is included in the compound of the invention. If the compound has an enantiomer, an enantiomer split from a racemic mixture is included in the compound of the invention. These isomers may be obtained as a single compound by a known synthesis method. These isomers each may be obtained as a single compound by separation using column chromatography and recrystallization.

The compound of the invention may be amorphous or crystalline. The compound of the invention may be a single crystal or a mixture of crystal polymorphism. The crystal can be produced by a known crystallization method. The compound of the invention may be a solvate (for example, a hydrate) or a non-solvate. The compound of the invention is optionally labeled with e.g., an isotope (for example, $^2$H, $^3$H, $^{13}$C, $^{14}$C, $^{18}$F, $^{35}$S, $^{125}$I,).

The compound of the invention contains a salt. The salt refers to a salt usually used in the field of organic chemistry. The compound of the invention having a carboxyl group reacts with a base to form a salt. The compound of the invention having an amino group or basic heterocyclic group reacts with an acid to form a salt.

The carboxyl group of the compound of the invention forms, for example, an alkali metal salt such as a sodium salt and a potassium salt; alkali earth metal salts such as a calcium salt and a magnesium salt; an ammonium salt; and an organic amine salt such as a trimethylamine salt, a triethylamine salt, a dicyclohexylamine salt, an ethanolamine salt, a diethanolamine salt, a triethanolamine salt, a procaine salt and a N,N'-dibenzylethylenediamine salt.

The amino group or basic heterocyclic group of the compound of the invention forms e.g., a mineral acid salt such as a hydrochloride, a sulfate, a nitrate, a phosphate and a perchlorate; organic acid salts such as an acetate, a formate, a maleate, a fumarate, a tartrate, a citrate, an ascorbate and a trifluoroacetate; methane sulfonate, isethionate, a benzenesulfonate and p-toluenesulfonate.

The compound of the invention has an excellent Aurora A selective inhibitory activity. Combination use of the compound of the invention and a microtubule-targeting drug brings about an enhanced antitumor effect. The method for enhancing an antitumor effect of a microtubule-targeting drug by the compound of the invention falls within the range of the present invention. Examples of the microtubule-targeting drug include microtubule-stabilizing drugs such as a taxane antitumor agent and epothilon anti-cancer/tumor agent; and microtubule-destabilizing drugs such as a vinca alkaloid, eribulin and halichondrin B. A microtubule-stabilizing drug is preferable and a taxane antitumor agent is more preferable. Examples of the taxane antitumor agent include paclitaxel, docetaxel and cabazitaxel. Paclitaxel and docetaxel are preferable. Examples of the taxane antitumor agent also include albumin-binding paclitaxel, albumin-binding docetaxel, docosahexaenoic acid-binding paclitaxel, polyglutamated paclitaxel, peptide-binding paclitaxel, interleukin-binding paclitaxel and antibody-binding paclitaxel. Examples of the epothilon antitumor agents include epothilon B and epothilon D. Examples of the vinca alkaloid include vinblastine and vincristine. The compound of the invention may be used in combination as an antitumor-effect enhancer. The molar ratio of the compound of the invention used per day relative to the microtubule-targeting drug (1 mole) is preferably 0.01 to 200 moles, more preferably 0.05 to 100 moles and further preferably 0.1 to 40 moles.

Examples of a cancer to be targeted by the method for enhancing an antitumor effect and a method for treating a tumor according to the present invention include epithelial cancers (for example, respiratory organ cancers, digestive organ cancers, cancers of the reproductive system, cancers of the secretion system), sarcomas, blood cancers, tumors of the central nervous system and tumors of the peripheral nervous system. The cancers to be targeted are preferably epithelial cancers and more preferably respiratory organ cancers, digestive organ cancers and cancers of the reproductive system.

Furthermore, the type of organ in which tumor is developed is not particularly limited. For example, head cervix cancer, esophagus cancer, stomach cancer, duodenal cancer, colon cancer, rectal cancer, hepatocarcinoma, bladder/bile duct cancer, biliary cancer, pancreatic cancer, lung cancer, breast cancer, ovarian cancer, uterine cervix cancer, uterine body cancer, kidney cancer, bladder cancer, prostatic cancer, testicular tumor, a bone/soft-tissue sarcoma, blood cancer, multiple myeloma, skin cancer, brain tumor and mesothelioma are targeted. Preferable types of cancers to be targeted by the method for enhancing an antitumor effect and the method for treating a tumor according to the present invention are stomach cancer, breast cancer, prostatic cancer, ovarian cancer, lung cancer and colon cancer, and more preferable types of cancers are stomach cancer, breast cancer, prostatic cancer, ovarian cancer, lung cancer and colon cancer. The method for enhancing an antitumor effect and the method for treating a tumor according to the present invention may be applied to humans and animals other than humans.

Furthermore, the method for enhancing an antitumor effect and the method for treating a tumor according to the present invention may also be applied to cancer resistant or refractory to an antitumor agent. The cancer resistant or refractory to an antitumor agent mentioned herein refers to those resistant or refractory to agents such as a microtubule-targeting drug (e.g., taxane antitumor agent, epothilon anticancer agent, a vinca alkaloid, eribulin), an alkylating agent, an antimetabolite, an antitumor antibiotic, a hormone-mimetic drug, a platinum-containing drug, a topoisomerase inhibitor, a cytokine, a molecular target therapeutic drug and non-specific immunostimulant. Cancers resistant or refractory to a combination use of these agents are also included. The cancer resistant or refractory to an antitumor agent is preferably a cancer resistant to a microtubule-targeting drug and more preferably a cancer resistant to a taxane antitumor agent. Examples of the cancer resistant to an antitumor agent include aforementioned ones including stomach cancer, breast cancer, prostatic cancer, ovarian cancer, lung cancer and colon cancer.

The administration schedule of the method for enhancing an antitumor effect and the method for treating a tumor according to the present invention is characterized in that, a microtubule-targeting drug is administered once per 7 days or more as one cycle, and the compound of the invention or a salt thereof is administered once or more per day for 4 or more consecutive days.

The administration order of the microtubule-targeting drug and the compound of the invention or a salt thereof in the cycle, in view of enhancement of an antitumor effect and suppression of a side effect, it is preferable that administration of the compound of the invention or a salt thereof is initiated at the same day on which a microtubule-targeting drug is administered or that administration of the compound of the invention or a salt thereof is initiated at 1 to 3 days after the administration of the microtubule-targeting drug, and more preferable that administration of the compound of the invention or a salt thereof is initiated at the same day on which a microtubule-targeting drug is administered or that administration of the compound of the invention or a salt thereof is initiated at 1 day after the administration of the microtubule-targeting drug.

With respect to the number of consecutive days of administration of the compound of the invention or a salt thereof in one cycle, if the days for administration is short, enhancement of the antitumor effect is insufficient. In contrast, if the days for administration days is long, development of a side effect is concerned and undesirable also in view of medical cost. In the case of 7 days as one cycle, the number of consecutive days of administration is preferably 4 or 5, and particularly preferably 4. In the case of 14 days as one cycle, the number of consecutive days of administration is preferably 4 to 10 and particularly preferably 4 to 7. In the case of 21 days as one cycle, the number of consecutive days of administration is preferably 4 to 12 and particularly preferably 4 to 10.

More specifically, the administration schedule of the method for enhancing an antitumor effect and the method for treating a tumor according to the present invention is preferably performed as follow: a microtubule-targeting drug is administered once per 7 to 21 days as one cycle, and the compound of the invention or a salt thereof is administered once or more per day for 4 to 12 consecutive days.

It is more preferable that a microtubule-targeting drug is administered on day 1 per 7 days as one cycle, administration of the compound of the invention or a salt thereof is initiated on day 1 or day 2, and the period of consecutive days of administration thereof is 4 or 5 days; a microtubule-targeting drug is administered on day 1 per 14 days as one cycle, administration of the compound of the invention or a salt thereof is initiated on day 1 or day 2, and the period of consecutive daily administration thereof is 4 to 10 days; or a microtubule-targeting drug is administered on day 1 per 21 days as one cycle, administration of the compound of the invention or a salt thereof is initiated on day 1 or day 2, and the period of consecutive daily administration thereof is 4 to 12 days.

It is particularly preferable that a microtubule-targeting drug is administered on day 1 per 7 days as one cycle, administration of the compound of the invention or a salt thereof is initiated on day 1 or day 2, and the period of consecutive daily administration thereof is 4 or 5 days; or a microtubule-targeting drug is administered on day 1 per 21 days as one cycle, administration of the compound of the invention or a salt thereof is initiated on day 1 or day 2, and the period of consecutive daily administration thereof is 4 to 12 days.

The administration route of a microtubule-targeting drug herein varies depending upon the type of agent; however, generally intravenous injection or intraperitoneal injection is made. In contrast, the administration route of the compound of the invention or a salt thereof is preferably oral.

As a pharmacological carrier contained in an agent (composition) containing the compound of the invention, various types of organic or inorganic carrier substances routinely used as materials for preparations are used. An excipient, a binder, a disintegrator, a lubricant and a coloring agent may be blended in a solid preparation. A solubilizing agent, a suspending agent, a tonicity agent, a buffer and a soothing agent may be blended in a liquid preparation. If necessary, additives for a preparation such as a preservative, an antioxidant, a sweetening agent and a stabilizing agent may be used.

In preparing an oral solid preparation, first, an excipient is added to the compound of the invention, e.g., another excipient, a binder, a disintegrator, a lubricant, a coloring agent and a flavoring agent are added as needed. Thereafter, the mixture is formed into tablets, coating tablets, granules, powders and capsules by a conventional method. In preparing an injection, first, e.g., a pH regulator, a buffer, a stabilizing agent, a tonicity agent and a local anesthetic drug are added to the compound of the invention. Thereafter, subcutaneous, intramuscular and intravenous injections may be prepared by a conventional method.

The amount of compound of the invention to be blended by the aforementioned administration method is 0.05 to 1000 mg in an oral agent, 0.01 to 500 mg in injection and 1 to 1000 mg in suppository. However, the amount may be increased depending upon e.g., the symptom of a patient and dosage form.

Furthermore, the dose of an agent having the aforementioned dosage form per administration day is usually 0.05 to 5000 mg per adult (body weight: 50 kg) per day and preferably 0.1 to 1000 mg. The number of administration times is preferably 1 to 3 per day. However, the dosage and the number of administration times may be changed depending upon e.g., the symptom, weight, age and sexuality of a patient.

In contrast, the dosage of a microtubule-targeting drug per administration time on an administration day varies depending upon e.g., the type of agent and type and stage of cancer. For example, in the case of paclitaxel, the dosage is 0.1 to 100 mg/kg and preferably 1 to 60 mg/kg.

Furthermore, in the case of docetaxel, the dosage is 0.1 to 100 mg/kg and preferably 1 to 30 mg/kg.

EXAMPLES

Now, the concurrent administration of the present invention will be described below by way of Examples, Production Examples and Reference Examples. Note that the method for enhancing an antitumor effect and the method for treating a tumor according to the present invention are not limited to these examples.

As the reagents used in Examples, Production Examples and Reference Examples, commercially available reagents were used unless otherwise specified. As silica gel column chromatography, Purif-pack (registered trade mark) SI manufactured by Moritex Corporation, KP-Sil (registered trade mark) Silica Prepacked column manufactured by Biotage AB, or HP-Sil (registered trade mark) Silica Prepacked column manufactured by Biotage AB was used. As basic silica gel column chromatography, Purif-pack (registered trade mark) NH manufactured by Moritex Corporation or KP-NH (registered trade mark) Prepacked column manufactured by Biotage AB was used. As a thin-film chromatography for fractionation, Kieselgel TM60F254, Art.5744 manufactured by Merck KGaA or NH2 silicagel 60F254 plate manufactured by Wako Pure Chemical Industries, Ltd. was used. As NMR spectrum, AL400 (400 MHz; JEOL Ltd. (JEOL)), Mercury 400 (400 MHz; Agilent Technologies) type spectrometer, or Inova 400 (400 MHz; Agilent Technologies) type spectrometer equipped with OMNMR probe (Protasis) was used. If tetramethylsilane is contained in a deuterated solvent, tetramethylsilane was used as an internal reference and in the other cases, NMR solvent was used as the internal reference for measurement. Total δ value was indicated by ppm. The microwave reaction was performed by use of Initiator 8 manufactured by Biotage AB.

Furthermore, as an LCMS spectrum, ACQUITY SQD (quadrupole type) manufactured by Waters was used.

Brevity codes stand for the followings.
s: Singlet
d: Doublet
t: Triplet
dd: Double doublet
m: Multiplet
br: Broad
brs: Broad singlet
DMSO-$d_6$: Deuterated dimethylsulfoxide
$CDCl_3$: Deuterated chloroform
$CD_3OD$: Deuterated methanol
Xantphos: 4,5-Bis(diphenylphosphino)-9,9-dimethylxanthene
$Pd_2(dba)_3$: Tris(dibenzylideneacetone)dipalladium (0)
$K_3PO_4$: Tripotassium phosphate
MsOH: Mesylic acid
AIBN: Azobisisobutyronitrile
HPMC: Hydroxypropylmethylcellulose Production Example 1

Synthesis of 1-(2,3-dichlorobenzoyl)-4-((5-fluoro-6-(5-methyl-1H-pyrazol-3-ylamino)pyridin-2-yl)methyl)piperidine-4-carboxylic acid (Compound 1)

(Step a) Synthesis of tert-butyl 4-((6-bromo-5-fluoropyridin-2-yl)methyl)-4-cyanopiperidine-1-carboxylate N-Boc-4-cyanopiperidine (5.35 g, 25.4 mmol) was dissolved in tetrahydrofuran (100 mL) and cooled to −78° C. Thereafter, to this, a cyclohexane solution (1.5 M, 16.5 mL, 24.8 mmol) of a lithium diisopropylamide/tetrahydrofuran complex was added while maintaining the inside temperature at −70° C. or less. The reaction mixture was stirred at −78° C. for 20 minutes. To the resultant reaction mixture, a THF solution (10 mL) of 2-bromo-6-(bromomethyl)-3-fluoropyridine (6.28 g, 23.4 mmol) was added while maintaining the inside temperature at −70° C. or less and then stirred at −78° C. for 20 minutes. To the reaction solution, a mixture of hydrochloric acid (5 M, 4.95 mL, 24.8 mmol) and a saturated aqueous ammonium chloride solution (95 mL) was added. After stirred at room temperature, the mixture was extracted with ethyl acetate. The extract was washed with saturated saline, dried over anhydrous sodium sulfate, then filtered and concentrated. A tar-like residue was dissolved in ethyl acetate (6 mL). To the mixture, heptane (50 mL) was added dropwise while stirring. A seed crystal was added and stirred at room temperature for one hour. To the resultant light yellow suspension solution, heptane (50 mL) was further added dropwise and stirred overnight. The resultant solid substance was collected by filtration, washed with a heptane solution of ethyl acetate and dried under reduced pressure to obtain the target product as an off-white solid substance (7.10 g, 17.8 mmol) (yield 76%). Note that the seed crystal was obtained from the tar-like residue by a purification method routinely used in silica gel column chromatography. Physical property values are shown below.

$^1$H-NMR ($CDCl_3$) δ: 7.45 (1H, t, J=8.1 Hz), 7.31 (1H, dd, J=8.1, 3.5 Hz), 4.16 (2H, br), 3.09-2.93 (2H, m), 3.04 (2H, s), 1.95-1.84 (2H, m), 1.68-1.57 (2H, m), 1.48 (9H, s); ESI-MS m/z 298, 300 (MH+).

(Step b) Synthesis of tert-butyl 4-((6-(1-tert-butyl-3-methyl-1H-pyrazol-5-ylamino)-5-fluoropyridin-2-yl)methyl)-4-cyanopiperidine-1-carboxylate The compound (6.37 g, 16.0 mmol) obtained in the above step a, 5-amino-1-t-butyl-3-methylpyrazole (2.42 g, 15.8 mmol), Xantphos (65.9 mg, 114 µmol), Pd$_2$(dba)$_3$ (51.1 mg, 55.8 µmol) and K$_3$PO$_4$ (3.63 g, 17.1 mmol) were placed in a reaction container and finally toluene (50 mL) was added, degassed and purged with argon. The obtained mixture was stirred at 110° C. for 8 hours and ethyl acetate (200 mL) was added at room temperature. The obtained mixture was washed with water and saturated saline, dried over sodium sulfate, then filtered and concentrated. The residue was dissolved in ethyl acetate (10 mL) and heptane (40 mL) was added while stirring at 75° C. and then stirred at room temperature overnight. The resultant solid substance was collected by filtration, washed with 15% ethyl acetate/heptane, and dried under reduced pressure to obtain the target compound (4.15 g, 8.81 mmol) (yield 56%) as a white solid substance. Physical property values are shown below.

$^1$H-NMR (CDCl$_3$) δ: 7.26 (1H, dd, J=10.7, 8.0 Hz), 6.74 (1H, dd, J=8.0, 3.2 Hz), 6.23-6.15 (2H, m), 4.19-3.92 (2H, m), 3.09-2.92 (2H, m), 2.85 (2H, s), 2.26 (3H, s), 1.95-1.86 (2H, m), 1.64 (9H, s), 1.58-1.48 (2H, m), 1.46 (9H, s); ESI-MS m/z 471 (MH+).

(Step c) Synthesis of 4-((6-(1-tert-butyl-3-methyl-1H-pyrazol-5-ylamino)-5-fluoropyridin-2-yl)methyl)-piperidine-4-carbonitrile The compound (4.11 g, 8.73 mmol) obtained in the above step b was dissolved in THF (33 mL). To this (placed in a water bath), MsOH (7.0 mL) was added. The resultant solution was stirred at room temperature for 2 hours and then the content was poured in water (160 mL). The obtained aqueous solution was washed with isopropyl ether (50 mL). Thereafter, to this, a 5 M sodium hydroxide (21.5 mL) was added and the mixture was extracted with ethyl acetate. The obtained ethyl acetate solution was washed with saturated saline and then dried over anhydrous sodium sulfate. After filtration, the filtrate was concentrated to obtain the target compound (3.09 g, 8.34 mmol) (yield 96%). Physical property values are shown below.

$^1$H-NMR (CDCl$_3$) δ: 7.22 (1H, dd, J=10.6, 8.0 Hz), 6.71 (1H, dd, J=8.0, 3.2 Hz), 6.25-6.16 (2H, m), 3.02-2.95 (2H, m), 2.91-2.84 (2H, m), 2.83 (2H, s), 2.21 (3H, s), 1.90-1.83 (2H, m), 1.61 (9H, s), 1.59-1.49 (2H, m); ESI-MS m/z 371 (MH+).

(Step d) Synthesis of 4-((6-(1-tert-butyl-3-methyl-1H-pyrazol-5-ylamino)-5-fluoropyridin-2-yl)methyl)-1-(2,3-dichlorobenzoyl)piperidine-4-carbonitrile To a mixture of the compound (3.65 g, 9.85 mmol) obtained in the above step c, 2,3-dichlorobenzoic acid (2.05 g, 10.8 mmol) and 1-hydroxybenzotriazole monohydrate (1.80 g, 13.3 mmol), acetonitrile (25 mL) was added and then WSC hydrochloride (2.05 g, 10.7 mmol) was added. The reaction mixture was stirred at room temperature overnight. Thereafter, to this, 1 M sodium hydroxide (30 mL) was added and stirred for 15 minutes. The obtained mixture was extracted with ethyl acetate. The ethyl acetate layer was washed with water, 1 M hydrochloric acid, water and saturated saline sequentially in this order. The resultant ethyl acetate solution was washed with anhydrous sodium sulfate, filtered and concentrated to obtain the target compound (5.55 g) (yield 100%) as a white solid substance. Physical property values are shown below. ESI-MS m/z 543, 545 (MH+).

(Step e) Synthesis of Compound 1

The compound (524 mg, 0.964 mmol) obtained in the above step d was dissolved in 1,4-dioxane (3 mL) and then 5 M hydrochloric acid (3 mL) was added. The mixture was heated at 150° C. for 10 minutes in a microwave reaction apparatus. The reaction mixture was concentrated under vacuum and the resultant residue was dissolved in chloroform and washed with saturated saline. The resultant chloroform solution was dried over anhydrous sodium sulfate, then filtered and concentrated under vacuum. The residue was purified by silica gel column chromatography (chloroform/methanol=100/0 to 90/10) and thereafter the obtained solid substance was reprecipitated with ethanol-ethyl acetate to obtain the target compound (290 mg, 0.573 mmol) (yield 59%) as a white solid substance. Physical property values are shown in Table 9.

Production Examples 2 to 13

In Production Examples 2 to 13, raw materials shown in Table 1 to Table 3 were used and synthesis was performed by a method according to Production Example 1. Physical property values are shown in Table 8 to Table 16.

TABLE 1

| Production Example | Compound Name | Raw Material 1 | Raw Material 2 | Raw Material 3 |
|---|---|---|---|---|
| 1 | 1-(2,3-dichlorobenzoyl)-4-((5-fluoro-6-(5-methyl-1H-pyrazol-3-ylamino)pyridin-2-yl)methyl)piperidine-4-carboxylic acid (compound 1) | [structure] | [structure] | [structure] |
| 2 | 1-(2-fluoro-3-trifluoromethylbenzoyl)-4-((5-fluoro-6-(5-methyl-1H-pyrazol-3-ylamino)pyridin-2-yl)methyl)piperidine-4-carboxylic acid (compound 2) | [structure] | [structure] | [structure] |

TABLE 1-continued

| Production Example | Compound Name | Raw Material 1 | Raw Material 2 | Raw Material 3 |
|---|---|---|---|---|
| 3 | 1-(3-chlorobenzoyl)-4-((5-fluoro-6-(5-methyl-1H-pyrazol-3-ylamino)pyridin-2-yl)methyl)piperidine-4-carboxylic acid (compound 3) | 6-(bromomethyl)-2-bromo-3-fluoropyridine | 3-methyl-1-tert-butyl-1H-pyrazol-5-amine | 3-chlorobenzoic acid |
| 4 | 1-(2,3-difluorobenzoyl)-4-((5-fluoro-6-(5-methyl-1H-pyrazol-3-ylamino)pyridin-2-yl)methyl)piperidine-4-carboxylic acid (compound 4) | 6-(bromomethyl)-2-bromo-3-fluoropyridine | 3-methyl-1-tert-butyl-1H-pyrazol-5-amine | 2,3-difluorobenzoic acid |
| 5 | 1-(2-fluoro-3-methoxybenzoyl)-4-((5-fluoro-6-(5-methyl-1H-pyrazol-3-ylamino)pyridin-2-yl)methyl)piperidine-4-carboxylic acid (compound 5) | 6-(bromomethyl)-2-bromo-3-fluoropyridine | 3-methyl-1-tert-butyl-1H-pyrazol-5-amine | 2-fluoro-3-methoxybenzoic acid |
| 6 | 1-(2-chlorobenzoyl)-4-((5-fluoro-6-(5-methyl-1H-pyrazol-3-ylamino)pyridin-2-yl)methyl)piperidine-4-carboxylic acid (compound 6) | 6-(bromomethyl)-2-bromo-3-fluoropyridine | 3-methyl-1-tert-butyl-1H-pyrazol-5-amine | 2-chlorobenzoic acid |

TABLE 2

| Production Example | Compound Name | Raw Material 1 | Raw Material 2 | Raw Material 3 |
|---|---|---|---|---|
| 7 | 1-(2-chloro-3-methylbenzoyl)-4-((5-fluoro-6-(5-methyl-1H-pyrazol-3-ylamino)pyridin-2-yl)methyl)piperidine-4-carboxylic acid (compound 7) | 6-(bromomethyl)-2-bromo-3-fluoropyridine | 3-methyl-1-tert-butyl-1H-pyrazol-5-amine | 2-chloro-3-methylbenzoic acid |
| 8 | 1-(2-chloro-3-fluorobenzoyl)-4-((5-fluoro-6-(5-methyl-1H-pyrazol-3-ylamino)pyridin-2-yl)methyl)piperidine-4-carboxylic acid (compound 8) | 6-(bromomethyl)-2-bromo-3-fluoropyridine | 3-methyl-1-tert-butyl-1H-pyrazol-5-amine | 2-chloro-3-fluorobenzoic acid |

TABLE 2-continued

| Production Example | Compound Name | Raw Material 1 | Raw Material 2 | Raw Material 3 |
|---|---|---|---|---|
| 9 | 1-(2,6-dichlorobenzoyl)-4-((5-fluoro-6-(5-methyl-1H-pyrazol-3-ylamino)pyridin-2-yl)methyl)piperidine-4-carboxylic acid (compound 9) | 2-bromo-6-(bromomethyl)-3-fluoropyridine | 1-tert-butyl-3-methyl-1H-pyrazol-5-amine | 2,6-dichlorobenzoic acid |
| 10 | 1-(3-chloro-2-fluorobenzoyl)-4-((5-fluoro-6-(1H-pyrazol-3-ylamino)pyridin-2-yl)methyl)piperidine-4-carboxylic acid (compound 10) | 2-bromo-6-(bromomethyl)-3-fluoropyridine | 1-tert-butyl-1H-pyrazol-5-amine | 3-chloro-2-fluorobenzoic acid |
| 11 | 1-(3-chloro-2-fluorobenzoyl)-4-((5-methoxy-6-(5-methyl-1H-pyrazol-3-ylamino)pyridin-2-yl)methyl)piperidine-4-carboxylic acid (compound 11) | 2-bromo-6-(bromomethyl)-3-methoxypyridine | 1-tert-butyl-3-methyl-1H-pyrazol-5-amine | 3-chloro-2-fluorobenzoic acid |

TABLE 3

| Production Example | Compound Name | Raw Material 1 | Raw Material 2 | Raw Material 3 |
|---|---|---|---|---|
| 12 | 1-(3-chloro-2-fluorobenzoyl)-4-((5-chloro-6-(5-methyl-1H-pyrazol-3-ylamino)pyridin-2-yl)methyl)piperidine-4-carboxylic acid (compound 12) | 2-chloro-6-(bromomethyl)-3-chloropyridine | 1-tert-butyl-3-methyl-1H-pyrazol-5-amine | 3-chloro-2-fluorobenzoic acid |
| 13 | 1-(3-chloro-2-fluorobenzoyl)-4-((5-fluoro-6-(5-methyl-1H-pyrazol-3-ylamino)pyridin-2-yl)methyl)piperidine-4-carboxylic acid (compound 13) | 2-bromo-6-(bromomethyl)-3-fluoropyridine | 1-tert-butyl-3-methyl-1H-pyrazol-5-amine | 3-chloro-2-fluorobenzoic acid |

Production Example 14

Synthesis of 1-(3-chloro-2-fluorobenzoyl)-4-((5-fluoro-6-(5-methyl-1H-pyrazol-3-ylamino)pyridin-2-yl)methyl)-N-methylpiperidine-4-carboxyamide (Compound 14)

To a mixture of Compound 13 (50 mg, 0.1 mmol) obtained in Production Example 13, 1-ethyl-3-(3-dimethylaminopropyl)carbodiimide hydrochloride (40 mg, 0.21 mmol), 1-hydroxybenzotriazole monohydrate (30 mg, 0.22 mmol), methylamine hydrochloride (25 mg, 0.37 mmol) and dimethylformamide (1 mL), triethylamine (0.05 mL) was added and stirred at room temperature for 13 hours. To the reaction mixture, water was added. The mixture was extracted with ethyl acetate and then dried over anhydrous magnesium sulfate, filtered and concentrated. The resultant residue was purified by HPLC to obtain the target compound (41 mg, 0.082 mmol) (yield 82%) as a white solid substance. Physical property values are shown in Table 8 to Table 16.

Production Examples 15 to 21

In Production Examples 15 to 21, raw materials shown in Table 4 and Table 5 were used and synthesis was performed by a method according to Production Example 14. Physical property values are shown in Table 8 to Table 16.

TABLE 4

| Production Example | Compound Name | Raw Material 4 |
|---|---|---|
| 14 | 1-(3-chloro-2-fluorobenzoyl)-4-((5-fluoro-6-(5-methyl-1H-pyrazol-3-ylamino)pyridin-2-yl)methyl)-N-methylpiperidine-4-carboxyamide (compound 14) | methylamine hydrochloride |
| 15 | 1-(3-chloro-2-fluorobenzoyl)-4-((5-fluoro-6-(5-methyl-1H-pyrazol-3-ylamino)pyridin-2-yl)methyl)piperidine-4-carboxyamide (compound 15) | ammonium chloride |
| 16 | 1-(3-chloro-2-fluorobenzoyl)-445-fluoro-6-(5-methyl-1H-pyrazol-3-ylamino)pyridin-2-yl(methyl)-N,N-dimethylpiperidine-4-carboxyamide (compound 16) | dimethylamine |
| 17 | 1-(3-chloro-2-fluorobenzoyl)-N-cyclopropyl-4-((5-fluoro-6-(5-methyl-1H-pyrazol-3-ylamino)pyridin-2-yl)methyl)piperidine-4-carboxyamide (compound 17) | cyclopropylamine |
| 18 | 1-(3-chloro-2-fluorobenzoyl)-N-cyclobutyl-4-((5-fluoro-6-(5-methyl-1H-pyrazol-3-ylamino)pyridin-2-yl)methyppiperidine-4-carboxyamide (compound 18) | cyclobutylamine |
| 19 | azetidin-1-yl(1-(3-chloro-2-fluorobenzoyl)-4-((5-fluoro-6-(5-methyl-1H-pyrazol-3-ylamino)pyridin-2-yl)methyl)piperidine-4-ypmethanone (compound 19) | azetidine hydrochloride |

TABLE 5

| Production Example | Compound Name | Raw Material 4 |
|---|---|---|
| 20 | (1-(3-chloro-2-fluorobenzoyl)-4-((5-fluoro-6-(5-methyl-1H-pyrazol-3-ylamino)pyridin-2-yl)methyl)piperidine-4-yl)(pynolidin-1-yl)methanone (compound 20) | pyrrolidine |
| 21 | (1-(3-chloro-2-fluorobenzoyl)-4-((5-fluoro-6-(5-methyl-1H-pyrazol-3-ylamino)pyridin-2-yl)methyl)piperidine-4-yl)(isoxazolidin-2-yl)methanone (compound 21) | isoxazolidine hydrochloride |

Production Example 22

Synthesis of (3-chloro-2-fluorophenyl)(4-((5-fluoro-6-(5-methyl-1H-pyrazol-3-ylamino)pyridin-2-yl)methyl)-4-(5-methyl-1,2,4-oxadiazol-3-yl)piperidin-1-yl)methanone (Compound 22)

(Step a) Synthesis of tert-butyl 4-((6-(1-tert-butyl-3-methyl-1H-pyrazol-5-ylamino)-5-fluoropyridin-2-yl)methyl)-4-(N'-hydroxycarbamimidoyl)piperidine-1-carboxylate The compound (50 g) obtained in Production Example 1 (Step b) was dissolved in ethanol (530 mL) at 60° C. The temperature of the mixture was returned to room temperature and an aqueous 50% hydroxylamine solution (65 mL) was added to the mixture and stirred at 60° C. for 46 hours. The reaction solution was added to distillation water and extracted with ethyl acetate. The organic layer was washed with distillation water and saturated saline, dried over sodium sulfate, and concentrated under vacuum to obtain the target compound (53 g, 106 mmol) (yield 100%). Physical property values are shown below.
ESI-MS m/z 504 (MH+).

(Step b) Synthesis of tert-butyl 4-((6-(1-tert-butyl-3-methyl-1H-pyrazol-5-ylamino)-5-fluoropyridin-2-yl)methyl)-4-(5-methyl-1,2,4-oxadiazol-3-yl)piperidine-1-carboxylate The compound (53 g, 106 mmol) obtained in the above step a was suspended in toluene (525 mL). To this, acetic anhydride (10 mL) was added, and stirred at room temperature for one hour and 20 minutes and then at 100° C. for 16 hours. To the reaction solution, ammonia water (175 mL), distillation water (500 mL) and ethyl acetate (500 mL) were sequentially added under ice bath and washed with saturated saline. The water layer was extracted with ethyl acetate. The organic layer was washed with saturated saline, dried over sodium sulfate and concentrated under vacuum to obtain the target compound (58 g) as a roughly purified product. Physical property values are shown below.
ESI-MS m/z 528 (MH+).

(Step c) Synthesis of N-(1-tert-butyl-3-methyl-1H-pyrazol-5-yl)-3-fluoro-6-((4-(5-methyl-1,2,4-oxadiazol-3-yl)piperidin-4-yl)methyl)pyridin-2-amine The compound (57 g) obtained in the above step b was dissolved in acetonitrile (210 mL). To this, mesylic acid (27 mL) was added under ice bath and stirred for one hour under ice bath and for 17 hours at room temperature. The reaction solution was added to distillation water (500 mL) under ice bath and washed with diisopropyl ether (500 mL). To the water layer, a 5 M sodium hydroxide (100 mL) was added under ice bath. The water layer was extracted with ethyl acetate. The organic layer was washed with saturated saline, dried over sodium sulfate and concentrated under vacuum to obtain the target compound (44 g, 102 mmol) (yield 91%). Physical property values are shown below.
ESI-MS m/z 428 (MH+).

(Step d) Synthesis of 4-((6-(1-tert-butyl-3-methyl-1H-pyrazol-5-ylamino)-5-fluoropyridin-2-yl)methyl)-4-(5-methyl-1,2,4-oxadiazol-3-yl)piperidin-1-yl)(3-chloro-2-fluorophenyl)methanone The compound (44 g) obtained in the above step c, 3-chloro-2-fluorobenzoic acid (20 g) and 1-hydroxybenzotriazole monohydrate (21 g) were dissolved in acetonitrile (343 mL). To this, 1-ethyl-3-(3-dimethylaminopropyl) carbodiimide hydrochloride (22 g) was added under ice bath and stirred at room temperature for 15 hours. To the reaction solution, 1 M sodium hydroxide (500 mL) was added. The mixture was extracted with ethyl acetate. The organic layer was washed with distillation water, 1 M hydrochloric acid, distillation water and saturated saline, dried over sodium sulfate and concentrated under vacuum. The residue was crystallized from heptane-ethyl acetate to obtain the target compound (52 g, 89 mmol) (yield 86%). Physical property values are shown below.
ESI-MS m/z 584, 586 (MH+).

(Step e) Synthesis of Compound 22

The compound (2.94 g, 5.03 mmol) obtained in the above step d was dissolved in 5 M hydrochloric acid (30 mL) and 2-propanol (20 mL) and heated at 100° C. for 2 hours. The reaction solution was ice-cooled. To this, water and 5 M sodium hydroxide were added to adjust pH to about 8. Thereafter, the reaction solution was extracted with ethyl acetate. The extract was washed with water and saturated saline, dried over sodium sulfate and concentrated under vacuum. The residue was purified by silica gel column chromatography (chloroform/methanol=100/0 to 95/5) to obtain the target compound (2.26 g, 4.28 mmol) (yield 85%). Physical property values are shown in Table 8 to Table 16.

Production Examples 23 to 27

In Production Examples 23 to 27, raw materials shown in Table 6 and Table 7 were used and synthesis was performed by a method according to Production Example 22. Physical property values are shown in Table 8 to Table 16.

TABLE 6

| Production Example | Compound Name | Raw Material 5 | Raw Material 6 | Raw Material 7 |
|---|---|---|---|---|
| 22 | (3-chloro-2-fluorophenyl)(4-((5-fluoro-6-(5-methyl-1H-pyrazol-3-ylamino)pyridin-2-yl)methyl)-4-(5-methyl-1,2,4-oxadiazol-3-yl)piperidine-1-yl)methanone (compound 22) | 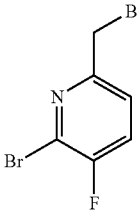 | 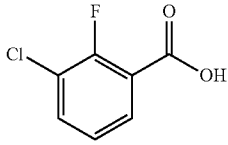 [SMILES: O=C(O)c1cccc(Cl)c1F] | acetic anhydride |
| 23 | (2,3-dichlorophenyl)(4-((5-fluoro-6-(5-methyl-1H-pyrazol-3-ylamino)pyridin-2-yl)methyl)-4-(5-methyl-1,2,4-oxadiazol-3-yl)piperidine-1-yl)methanone (compound 23) | 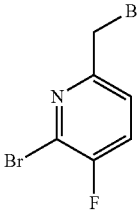 | 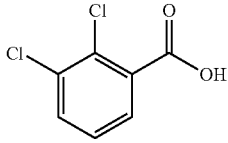 [SMILES: O=C(O)c1cccc(Cl)c1Cl] | acetic anhydride |
| 24 | (3-chloro-2-fluorophenyl)(4-((5-fluoro-6-(5-methyl-1H-pyrazol-3-ylamino)pyridin-2-yl)methyl)-4-(1,2,4-oxadiazol-3-yl)piperidine-1-yl)methanone (compound 24) | 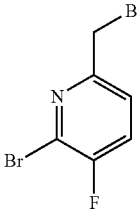 | 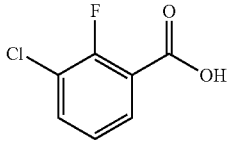 [SMILES: O=C(O)c1cccc(Cl)c1F] | triethyl orthoformate |
| 25 | (3-chloro-2-fluorophenyl)(4-((5-fluoro-6-(5-methyl-1H-pyrazol-3-ylamino)pyridin-2-yl)methyl)-4-(5-(trifluoromethyl)-1,2,4-oxadiazol-3-yl)piperidine-1-yl)methanone (compound 25) | 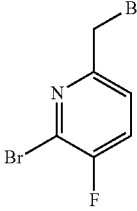 | 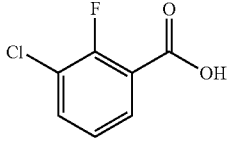 [SMILES: O=C(O)c1cccc(Cl)c1F] | trifluoroacetic anhydride |

TABLE 7

| Production Example | Compound Name | Raw Material 5 | Raw Material 6 | Raw Material 7 |
|---|---|---|---|---|
| 26 | (3-chloro-2-fluorophenyl)(4-((5-methoxy-6-(5-methyl-1H-pyrazol-3-ylamino)pyridin-2-yl)methyl)-4-(5-methyl-1,2,4-oxadiazol-3-yl)piperidine-1-yl)methanone (compound 26) | 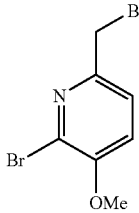 | 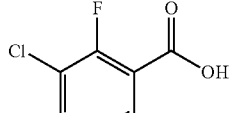 | acetic anhydride |
| 27 | (3-chloro-2-fluorophenyl)(4-((5-chloro-6-(5-methyl-1H-pyrazol-3-ylamino)pyridin-2-yl)methyl)-4-(5-methyl-1,2,4-oxadiazol-3-yl)piperidine-1-yl)methanone (compound 27) | 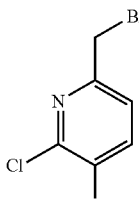 | 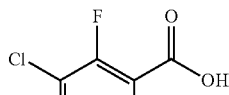 | acetic anhydride |

Production Example 28

Synthesis of (3-chloro-2-fluorophenyl)(4-((5-fluoro-6-(5-methyl-1H-pyrazol-3-ylamino)pyridin-2-yl)methyl)-4-(5-methyl-1,3,4-oxadiazol-3-yl)piperidin-1-yl)methanone (Compound 28)

(Step a) synthesis of tert-butyl 2-(1-(3-chloro-2-fluorobenzoyl)-4-((5-fluoro-6-(5-methyl-1H-pyrazol-3-ylamino)pyridin-2-yl)methyl)piperidine-4-carbonyl) hydrazine carboxylate Compound 13 (62 mg, 0.13 mmol) obtained in Production Example 13, tert-butoxycarbonyl hydrazide (25 mg, 0.19 mmol) and 1-hydroxybenzotriazole monohydrate (30 mg, 0.22 mmol) were dissolved in dimethylformamide (3 mL). To this mixture, (1-ethyl-3-(3-dimethylaminopropyl)carbodiimide hydrochloride (41 mg, 0.22 mmol) was added and stirred at room temperature for 3 hours. To the reaction mixture, water was added. The resultant reaction mixture was extracted with ethyl acetate and then dried over anhydrous magnesium sulfate, filtered and concentrated. The obtained residue was purified by silica gel column chromatography (chloroform/methanol=100/0 to 95/5) to obtain the target compound (70 mg, 0.12 mmol) (yield 92%). Physical property values are shown below.
ESI-MS m/z 604, 606 (MH+).

(Step b) Synthesis of Compound 28

The compound (70 mg, 0.12 mmol) obtained in the above step a was dissolved in chloroform (4 mL). To this, trifluoroacetic acid (2 mL) was added and stirred at room temperature for 3 hours. The reaction mixture was concentrated. Then, to the residue, chloroform and a saturated aqueous sodium hydrogen carbonate solution were added and separate into layers. Extract with chloroform was dried over anhydrous magnesium sulfate, filtered and concentrated. To the obtained residue, toluene (4 mL) and orthoethyl acetate (0.5 mL) were added and stirred while heating at 110° C. for 2 hours. To the reaction solution, water was added at room temperature. The resultant solution was extracted with ethyl acetate. The extract was dried over anhydrous magnesium sulfate, filtered and concentrated. The obtained residue was purified by silica gel column chromatography (chloroform/methanol=100/0 to 90/10) to obtain the target compound (39 mg, 0.077 mmol) (yield 64%). Physical property values are shown in Table 8 to Table 16.

Production Example 29

Synthesis of (3-chloro-2-fluorophenyl)(4-((5-fluoro-6-(5-methyl-1H-pyrazol-3-ylamino)pyridin-2-yl)methyl)-4-(3-methyl-1,2,4-oxadiazol-5-yl)piperidin-1-yl)methanone (Compound 29)

To a mixture of Compound 13 (49 mg, 0.10 mmol) obtained in Production Example 13, 1-ethyl-3-(3-dimethylaminopropyl)carbodiimide hydrochloride (38 mg, 0.20 mmol), 1-hydroxybenzotriazole monohydrate (27 mg, 0.20 mmol), acetamidoxime (15 mg, 0.20 mmol) and dimethylformamide (1 mL), diisopropylethylamine (0.07 mL) was added and stirred at room temperature for 7 hours. To the reaction mixture, water was added and the mixture was extracted with ethyl acetate and then dried over anhydrous sodium sulfate, filtered and concentrated. To the resultant crude product, 1,4-dioxane (1 mL) was added. The mixture was stirred and irradiated with a microwave reaction apparatus (BiotageInitiator8) at 120° C. for 6 hours and concentrated. The obtained residue was purified by HPLC to obtain the target compound (29 mg, 0.055 mmol) (yield 55%) as a light orange solid substance. Physical property values are shown in Table 8 to Table 16.

TABLE 8

| Example | Structural Formula | Physical Value |
|---|---|---|
| Production Example 1 | 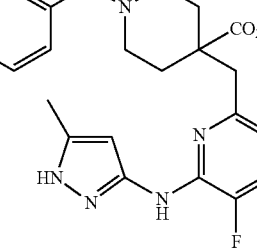 | $^1$H-NMR (DMSO-D$_6$) δ: 10.05 (1H, brs), 7.70-7.65 (1H, m), 7.59-7.54 (1H, m), 7.46-7.29 (2H, m), 6.72-6.68 (1H, m), 6.30-6.29 (1H, m), 4.23-4.18 (1H, m), 3.26-3.20 (1H, m), 3.09-2.95 (4H, m), 2.27-2.26 (3H, m), 2.05-2.00 (1H, m), 1.90-1.83 (1H, m), 1.67-1.49 (2H, m); ESI-MS m/z 506, 508 (MH+). |
| Production Example 2 | 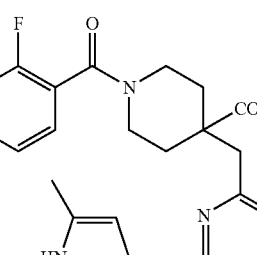 | $^1$H-NMR (DMSO-D$_6$) δ: (1H, brs), 7.86 (1H, t, J = 7.7 Hz), 7.75 (1H, t, J = 7.7 Hz), 7.57 (1H, dd, J = 11.1, 8.2 Hz), 7.48 (1H, t, J = 7.7 Hz), 6.70 (1H, dd, J = 8.2, 2.8 Hz), 6.29 (1H, s), 4.20 (1H, d, J = 13.7 Hz), 3.36 (1H, d, J = 13.7 Hz), 3.11-2.98 (4H, m), 2.25 (3H, s), 2.02 (1H, d, J = 13.7 Hz), 1.91-1.87 (1H, m), 1.64-1.50 (2H, m); ESI-MS m/z 524 (MH+). |
| Production Example 3 | 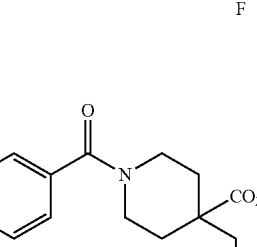 | $^1$H-NMR (CDCl$_3$) δ: 7.38-7.00 (5H, m), 6.70-6.58 (1H, m), 5.68 (1H, s), 4.60-4.45 (1H, m), 3.40-3.09 (4H, m), 3.04-2.89 (1H, m), 2.40-2.10 (2H, m), 2.24 (3H, s), 1.71-1.42 (2H, m)m); ESI-MS m/z 472, 474 (MH+). |

TABLE 9

| Example | Structural Formula | Physical Value |
|---|---|---|
| Production Example 4 | | $^1$H-NMR (CDCl$_3$) δ: 7.30-6.95 (4H, m), 6.68-6.60 (1H, m), 5.69 (1H, s), 4.64-4.55 (1H, m), 3.42-3.15 (4H, m), 3.03-2.90 (1H, m), 2.50-2.30 (1H, m), 2.28-2.16 (1H, m), 2.23 (3H, s), 1.58-1.40 (2H, m); ESI-MS m/z 474 (MH+). |

TABLE 9-continued

| Example | Structural Formula | Physical Value |
|---|---|---|
| Production Example 5 | 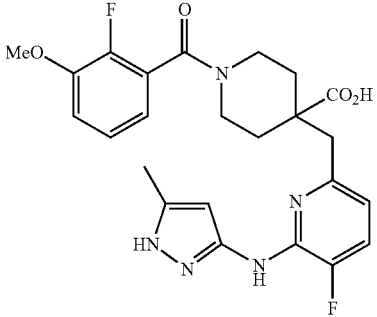 [SMILES: COc1cccc(C(=O)N2CCC(Cc3ccc(F)c(Nc4cc(C)[nH]n4)n3)(C(=O)O)CC2)c1F] | $^1$H-NMR (DMSO-D$_6$) δ: 9.23 (1H, brs), 7.73-7.65 (1H, m), 7.58-7.46 (2H, m), 7.23-7.13 (1H, m), 6.83-6.79 (1H, m), 6.60 (1H, s), 4.51-4.40 (1H, m), 4.17 (3H, s), 3.75-3.36 (1H, m), 3.52-3.30 (2H, m), 3.20 (2H, s), 2.46 (3H, s), 2.39-2.27 (1H, m), 2.23-2.12 (1H, m), 1.97-1.78 (2H, m); ESI-MS m/z 486 (MH+). |
| Production Example 6 | 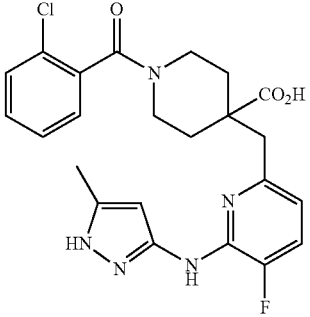 [SMILES: Cc1cc(Nc2nc(CC3(C(=O)O)CCN(C(=O)c4ccccc4Cl)CC3)ccc2F)n[nH]1] | $^1$H-NMR (CDCl$_3$) δ: 7.38-7.02 (4H, m), 6.68-6.59 (1H, m), 5.68 (1H, s), 4.66-4.56 (1H, m), 3.33-3.09 (4H, m), 3.03-2.91 (1H, m), 2.40-2.25 (1H, m), 2.24 (3H, s), 2.20-2.10 (1H, m), 1.62-1.40 (2H, m); ESI-MS m/z 472, 474 (MH+). |
| Production Example 7 | 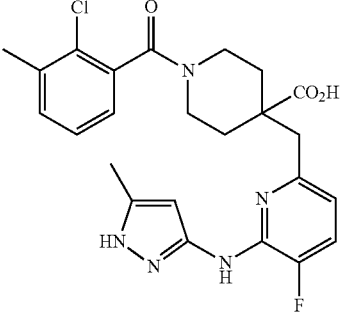 [SMILES: Cc1cc(Nc2nc(CC3(C(=O)O)CCN(C(=O)c4cccc(C)c4Cl)CC3)ccc2F)n[nH]1] | $^1$H-NMR (DMSO-D$_6$) δ: 9.24 (1H, brs), 7.75-7.43 (4H, m), 6.87-6.79 (1H, m), 6.60 (1H, s), 4.54-4.41 (1H, m), 3.71-3.29 (3H, m), 3.20 (2H, s), 2.66 (3H, s), 2.46 (3H, s), 2.39-2.28 (1H, m), 2.22-2.12 (1H, m), 2.00-1.80 (2H, m); ESI-MS m/z 486, 488 (MH+). |

TABLE 10

| Example | Structural Formula | Physical Value |
|---|---|---|
| Production Example 8 | 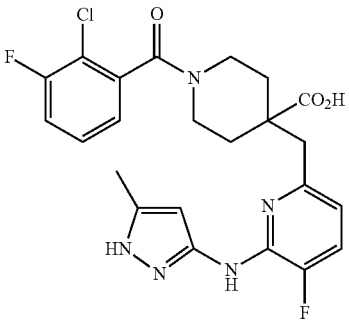 | $^1$H-NMR (DMSO-D$_6$) δ: 9.23 (1H, brs), 7.82-7.63 (3H, m), 7.60-7.48 (1H, m), 6.85-6.79 (1H, m), 6.66-6.56 (1H, m), 4.56-4.44 (1H, m), 3.72-3.29 (3H, m), 3.24-3.12 (2H, m), 2.47 (3H, s), 2.41-2.29 (1H, m), 2.24-2.12 (1H, m), 2.01-1.80 (2H, m); ESI-MS m/z 490, 492 (MH+). |

TABLE 10-continued

| Example | Structural Formula | Physical Value |
|---|---|---|
| Production Example 9 | 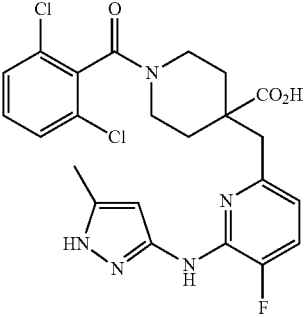 [SMILES: Cc1cc(Nc2nc(CC3(C(=O)O)CCN(C(=O)c4c(Cl)cccc4Cl)CC3)ccc2F)n[nH]1] | ¹H-NMR (DMSO-D$_6$) δ: 9.23 (1H, brs), 7.89-7.63 (4H, m), 6.85-6.79 (1H, m), 6.61 (1H, s), 4.58-4.48 (1H, m), 3.72-3.30 (3H, m), 3.26-3.14 (2H, m), 2.47 (3H, s), 2.41-2.30 (1H, m), 2.27-2.16 (1H, m), 2.01-1.85 (2H, m); ESI-MS m/z 506, 508 (MH+). |
| Production Example 10 | 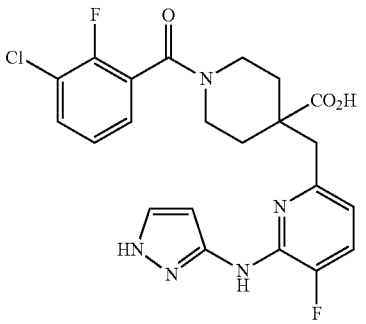 [SMILES: O=C(c1cccc(Cl)c1F)N1CCC(Cc2ccc(F)c(Nc3cc[nH]n3)n2)(C(=O)O)CC1] | ¹H-NMR (DMSO-D$_6$) δ: 9.07 (1H, brs), 7.65 (1H, td, J = 7.8, 2.0 Hz), 7.49 (1H, d, J = 2.0 Hz), 7.41-7.35 (2H, m), 7.29 (1H, t, J = 7.8 Hz), 6.53-6.51 (2H, m), 4.19 (1H, d, J = 13.7 Hz), 3.34 (1H, d, J = 13.7 Hz), 3.07-3.02 (2H, m), 2.90 (1H, d, J = 13.4 Hz), 2.87 (1H, d, J = 13.4 Hz), 2.03 (1H, d, J = 13.4 Hz), 1.88 (1H, d, J = 13.4 Hz), 1.61-1.48 (2H, m); ESI-MS m/z 476, 478 (MH+). |
| Production Example 11 | 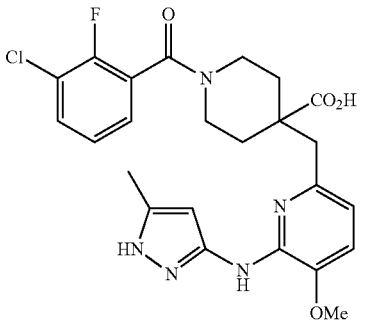 [SMILES: COc1ccc(CC2(C(=O)O)CCN(C(=O)c3cccc(Cl)c3F)CC2)nc1Nc1cc(C)[nH]n1] | ¹H-NMR (DMSO-D$_6$) δ: 10.68 (1H, brs), 7.67 (1H, t, J = 7.6 Hz), 7.51 (1H, d, J = 8.0 Hz), 7.37 (1H, t, J = 6.7 Hz), 7.30 (1H, t, J = 7.6 Hz), 6.85 (1H, d, J = 8.0 Hz), 6.14 (1H, s), 4.32-4.20 (1H, m), 3.97 (3H, s), 3.43-3.32 (1H, m), 3.15-2.96 (4H, m), 2.27 (3H, s), 2.12-2.03 (1H, m), 1.99-1.87 (1H, m), 1.70-1.45 (2H, m); ESI-MS m/z 502, 504 (MH+). |

TABLE 11

| Example | Structural Formula | Physical Value |
|---|---|---|
| Production Example 12 | 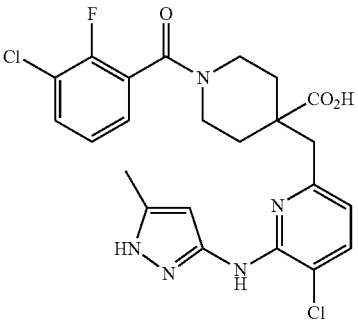 [SMILES: Cc1cc(Nc2nc(CC3(C(=O)O)CCN(C(=O)c4cccc(Cl)c4F)CC3)ccc2Cl)n[nH]1] | ¹H-NMR (CDCl$_3$) δ: 7.55 (1H, d, J = 8.7 Hz), 7.42-7.35 (1H, m), 7.34 (1H, s), 7.25-7.16 (2H, m), 6.70-6.61 (1H, m), 5.67 (1H, s), 4.61-4.53 (1H, m), 3.40-3.09 (4H, m), 3.05-2.94 (1H, m), 2.37-2.10 (2H, m), 2.25 (3H, s), 1.61-1.40 (2H, m); ESI-MS m/z 506, 508 (MH+). |

TABLE 11-continued

| Example | Structural Formula | Physical Value |
|---|---|---|
| Production Example 13 | 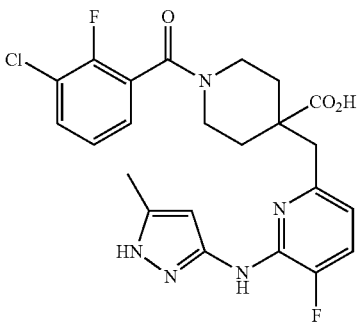 [SMILES: Cc1cc(Nc2nc(CC3(C(=O)O)CCN(C(=O)c4cccc(Cl)c4F)CC3)ccc2F)n[nH]1] | $^1$H-NMR (DMSO-D$_6$) δ: 10.13 (1H, brs), 7.68-7.64 (1H, m), 7.58 (1H, dd, J = 11.0 Hz, 8.0 Hz), 7.38-7.35 (1H, m), 7.29 (1H, t, J = 8.0 Hz), 6.73-6.70 (1H, m), 6.29 (1H, s), 4.21-4.18 (1H, m), 3.38-3.34 (1H, m), 3.09-2.99 (4H, m), 2.27 (3H, s), 2.03-1.99 (1H, m), 1.89-1.87 (1H, m), 1.63-1.49 (1H, m); ESI-MS m/z 490, 492 (MH+). |
| Production Example 14 | 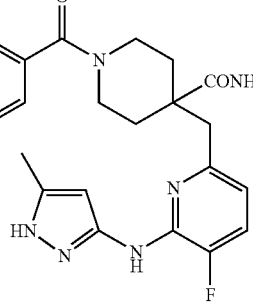 | $^1$H-NMR (DMSO-D$_6$) δ: 11.79 (1H, s), 8.68 (0.5H, s), 7.68-7.61 (2H, m), 7.36-7.27 (3H, m), 6.41 (1.5H, s), 4.06-4.01 (1H, m), 3.32 (3H, s), 3.30-3.28 (1H, m), 3.20-3.16 (1H, m), 3.09-3.03 (1H, m), 2.87-2.82 (2H, m), 2.13 (3H, s), 2.05-2.01 (1H, m), 1.91-1.87 (1H, m), 1.61-1.49 (2H, m); ESI-MS m/z 503, 505 (MH+). |

TABLE 12

| Example | Structural Formula | Physical Value |
|---|---|---|
| Production Example 15 | 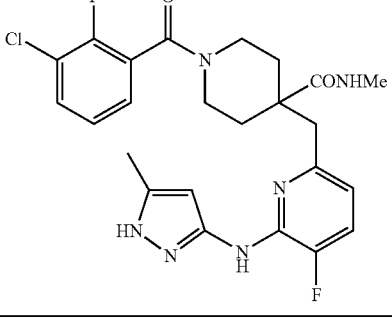 | $^1$H-NMR (DMSO-D$_6$) δ: 11.79 (1H, brs), 8.66 (0.5H, brs), 7.65 (1H, td, J = 7.7, 1.6 Hz), 7.37-7.26 (4H, m), 6.98 (1H, s), 6.48 (1H, brs), 6.41 (0.5H, brs), 4.09-4.04 (1H, m), 3.31-3.28 (1H, m), 3.21-3.18 (1H, m), 3.12-3.07 (1H, m), 2.86-2.83 (2H, m), 2.13 (3H, s), 2.06-2.03 (1H, m), 1.92-1.89 (1H, m), 1.61-1.48 (2H, m); ESI-MS m/z 489, 491 (MH+). |
| Production Example 16 | 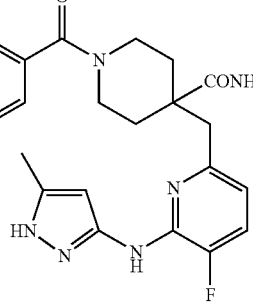 | $^1$H-NMR (DMSO-D$_6$) δ: 11.74 (1H, brs), 7.65 (1H, td, J = 7.7, 1.6 Hz), 7.37-7.26 (3H, m), 6.49-6.47 (1H, m), 6.17 (1H, brs), 4.13-4.10 (1H, m), 3.30-3.28 (1H, m), 3.15-2.86 (10H, m), 2.23-2.19 (1H, m), 2.15 (3H, s), 2.11-2.07 (1H, m), 1.66-1.50 (2H, m); ESI-MS m/z 517, 519 (MH+30). |

TABLE 12-continued

| Example | Structural Formula | Physical Value |
|---|---|---|
| Production Example 17 | 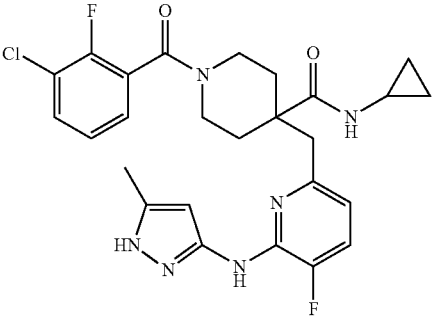 [SMILES: Cc1cc(Nc2nc(CC3(C(=O)NC4CC4)CCN(C(=O)c4cccc(Cl)c4F)CC3)ccc2F)n[nH]1] | $^1$H-NMR (DMSO-D$_6$) δ: 11.81 (1H, brs), 7.68-7.63 (2H, m), 7.38-7.26 (3H, m), 6.41 (1H, brs), 4.08-4.04 (1H, m), 3.29-3.27 (1H, m), 3.14-3.02 (2H, m), 2.84 (2H, brs), 2.51-2.46 (1H, m), 2.12 (3H, s), 2.09-2.05 (1H, m), 1.95-1.92 (1H, m), 1.60-1.47 (2H, m), 0.53-0.48 (2H, m), 0.34-0.31 (2H, m); ESI-MS m/z 529, 531 (MH+30). |

TABLE 13

| Example | Structural Formula | Physical Value |
|---|---|---|
| Production Example 18 | 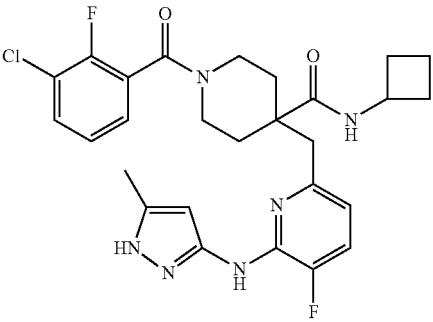 [SMILES: Cc1cc(Nc2nc(CC3(C(=O)NC4CCC4)CCN(C(=O)c4cccc(Cl)c4F)CC3)ccc2F)n[nH]1] | $^1$H-NMR (DMSO-D$_6$) δ: 11.80 (1H, brs), 8.67 (0.5H, brs), 7.71 (1H, d, J = 7.6 Hz), 7.66 (1H, td, J = 7.8 Hz), 6.38 (1.5 Hz), 7.39-7.29 (2H, m), 7.28 (1H, t, J = 7.8 Hz), 6.38 (1.5H, brs), 4.17-4.15 (1H, brm), 4.06-4.03 (1H, brm), 3.31-3.29 (1H, m), 3.19-3.16 (1H, m), 3.07-3.02 (1H, m), 2.83 (2H, brs), 2.13 (3H, s), 1.94-1.93 (1H, m), 2.07-2.05 (1H, m), 2.00-1.96 (2H, m), 1.87-1.78 (2H, m), 1.63-1.49 (4H, m); ESI-MS m/z 543, 545 (MH+). |
| Production Example 19 | 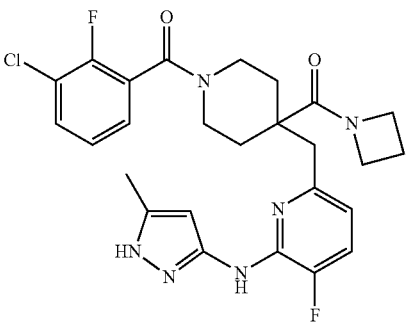 [SMILES: Cc1cc(Nc2nc(CC3(C(=O)N4CCC4)CCN(C(=O)c4cccc(Cl)c4F)CC3)ccc2F)n[nH]1] | $^1$H-NMR (DMSO-D$_6$) δ: 8.99 (1H, brs), 7.66 (1H, td, J = 7.7, 1.5 Hz), 7.42-7.35 (2H, m), 7.29 (1H, t, J = 7.7 Hz), 6.54-6.51 (1H, m), 6.27 (1H, brs), 4.14-4.10 (1H, m), 3.87-3.72 (4H, m), 3.36-3.34 (1H, m), 3.13-3.00 (2H, m), 2.82 (2H, s), 2.15 (3H, s), 2.08-2.02 (1H, m), 1.95-1.88 (3H, m), 1.56-1.45 (2H, m); ESI-MS m/z 529, 531 (MH+). |
| Production Example 20 | 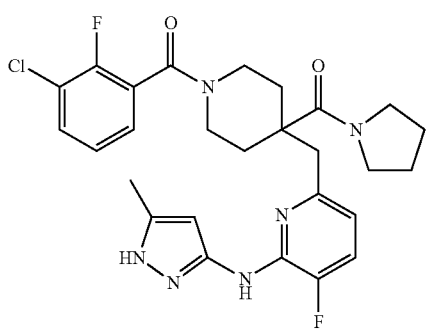 [SMILES: Cc1cc(Nc2nc(CC3(C(=O)N4CCCC4)CCN(C(=O)c4cccc(Cl)c4F)CC3)ccc2F)n[nH]1] | $^1$H-NMR (DMSO-D$_6$) δ: 11.80 (1H, brs), 8.69 (1H, brs), 7.65 (1H, td, J = 7.7, 1.7 Hz), 7.38-7.29 (2H, m), 7.29 (1H, t, J = 7.7 Hz), 6.57-6.36 (2H, m), 4.14-4.10 (1H, m), 3.34-3.27 (5H, m), 3.15-3.02 (2H, m), 2.87 (2H, brs), 2.26-2.22 (1H, m), 2.12-2.10 (1H, m), 2.15 (3H, s), 1.65-1.53 (6H, m); ESI-MS m/z 543, 545 (MH+). |

TABLE 14

| Example | Structural Formula | Physical Value |
|---|---|---|
| Production Example 21 | 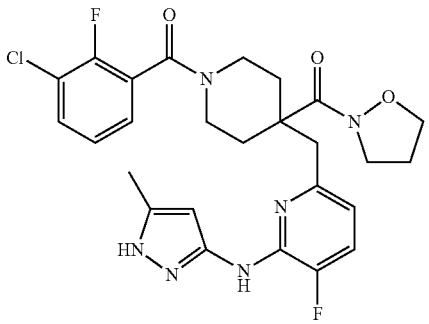 [SMILES: Cc1cc(Nc2nc(CC3(C(=O)N4CCCO4)CCN(C(=O)c4cccc(Cl)c4F)CC3)ccc2F)n[nH]1] | ¹H-NMR (CDCl₃) δ: 7.42 (1H, ddd, J = 8.0, 7.1, 1.7 Hz), 7.23 (1H, brs), 7.17 (1H, dd, J = 10.5, 8.0 Hz), 7.12 (1H, dd, J = 8.0, 7.1 Hz), 7.07 (1H, brs), 6.53-6.50 (1H, m), 5.85 (1H, s), 4.48-4.45 (1H, m), 4.13-4.07 (2H, m), 3.84-3.73 (2H, m), 3.39-3.37 (2H, brm), 3.24-3.12 (2H, m), 3.03 (1H, d, J = 13.7 Hz), 2.52 (1H, d, J = 13.7 Hz), 2.37-2.29 (3H, m), 2.26 (3H, s), 1.67-1.42 (2H, m); ESI-MS m/z 545, 547 (MH+). |
| Production Example 22 | 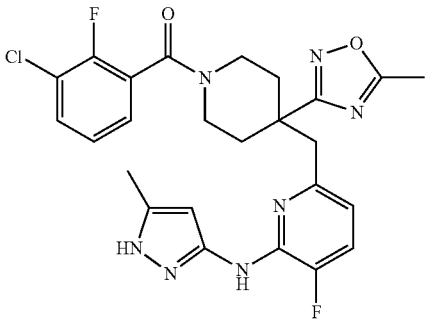 | ¹H-NMR (CDCl₃) δ: 7.45 (1H, ddd, J = 8.2, 6.6, 1.3 Hz), 7.34-7.15 (1H, m), 7.15 (1H, t, J = 7.7 Hz), 7.14 (1H, dd, J = 10.6, 8.1 Hz), 7.03 (1H, brs), 6.42-6.31 (1H, m), 5.98 (1H, s), 4.63-4.52 (1H, m), 3.50-3.38 (1H, m), 3.17 (1H, brs), 3.10 (1H, d, J = 13.2 Hz), 3.05 (1H, d, J = 13.2 Hz), 3.02-2.89 (1H, m), 2.53-2.39 (1H, m), 2.51 (3H, s), 2.37-2.26 (1H, m), 2.31 (3H, s), 1.96-1.66 (2H, m); ESI-MS m/z 528, 530 (MH+30). |
| Production Example 23 | 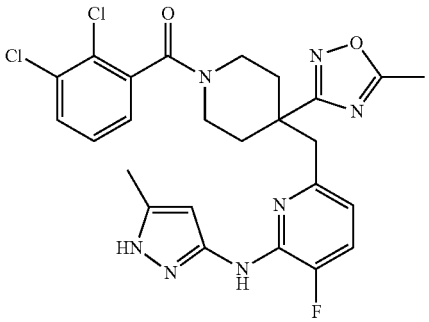 | ¹H-NMR (CDCl₃) δ: 7.50-7.47 (1H, m), 7.28-7.23 (1H, m), 7.16-7.08 (2H, m), 6.38-6.33 (1H, m), 6.04-5.99 (1H, m), 4.60 (1H, d, J = 13.9 Hz), 3.37-3.29 (1H, m), 3.19-3.03 (3H, m), 3.01-2.91 (1H, m), 2.52-2.43 (4H, m), 2.32-2.27 (4H, m), 1.98-1.84 (2H, m); ESI-MS m/z 544, 546 (MH+). |

TABLE 15

| Example | Structural Formula | Physical Value |
|---|---|---|
| Production Example 24 | 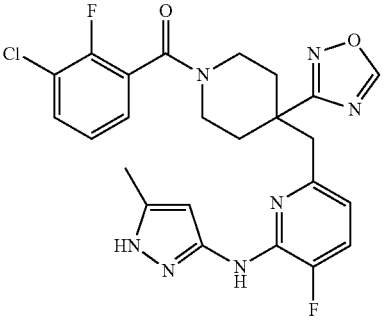 [SMILES: Cc1cc(Nc2nc(CC3(c4ncon4)CCN(C(=O)c4cccc(Cl)c4F)CC3)ccc2F)n[nH]1] | ¹H-NMR (CDCl₃) δ: 8.73 (1H, s), 7.46 (1H, t, J = 7.5 Hz), 7.32-7.10 (3H, m), 7.00 (1H, s), 6.37 (1H, brs), 5.92 (1H, s), 4.63-4.52 (1H, m), 3.52-3.40 (1H, m), 3.27-2.88 (4H, m), 2.54-2.43 (1H, m), 2.40-2.30 (1H, m), 2.31 (3H, s), 2.02-1.68 (2H, m); ESI-MS m/z 514, 516 (MH+30). |

TABLE 15-continued

| Example | Structural Formula | Physical Value |
|---|---|---|
| Production Example 25 | 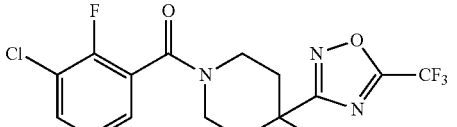 | $^1$H-NMR (CDCl$_3$) δ: 7.46 (1H, ddd, J = 8.3, 6.7, 1.2 Hz), 7.26-7.17 (2H, m), 7.16 (1H, t, J = 7.7 Hz), 7.12 (1H, dd, J = 10.6, 8.0 Hz), 6.28 (1H, dd, J = 7.0, 2.4 Hz), 6.15 (1H, brs), 4.64-4.50 (1H, m), 3.60-3.43 (1H, m), 3.24-2.92 (4H, m), 2.56-2.45 (1H, m), 2.42-2.34 (1H, m), 2.32 (3H, s), 2.09-1.81 (2H, m); ESI-MS m/z 582, 584 (MH+). |
| Production Example 26 | 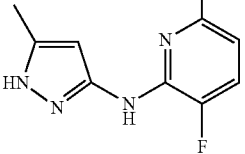 | $^1$H-NMR (CDCl$_3$) δ: 7.44 (1H, ddd, J = 8.3, 6.5, 1.0 Hz), 7.30-7.10 (3H, m), 6.86 (1H, d, J = 8.1 Hz), 6.39 (1H, brs), 5.72 (1H, s), 4.64-4.49 (1H, m), 3.86 (3H, s), 3.49-3.35 (1H, m), 3.28-2.85 (2H, m), 3.06 (2H, s), 2.52 (3H, s), 2.49-2.39 (1H, m), 2.37-2.28 (1H, m), 2.27 (3H, s), 1.94-1.64 (2H, m); ESI-MS m/z 540, 542 (MH+). |
| Production Example 27 | 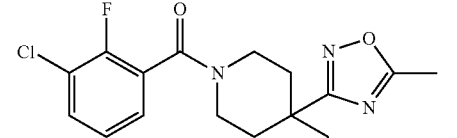 | $^1$H-NMR (CDCl$_3$) δ: 7.50-7.39 (2H, m), 7.36-7.09 (2H, m), 6.42-6.30 (1H, m), 6.04-5.89 (1H, m), 4.61-4.50 (1H, m), 3.50-3.39 (1H, m), 3.29-2.88 (4H, m), 2.52-2.38 (4H, m), 2.36-2.20 (4H, m), 1.95-1.78 (2H, m); ESI-MS m/z 544, 546 (MH+). |

TABLE 16

| Example | Structural Formula | Physical Value |
|---|---|---|
| Production Example 28 | 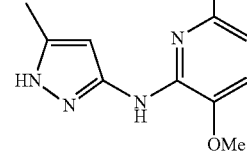 | $^1$H-NMR (CDCl$_3$) δ: 7.46 (1H, ddd, J = 8.3, 6.7, 1.3 Hz), 7.33-7.20 (2H, brm), 7.16 (1H, t, J = 7.5 Hz), 7.14 (1H, dd, J = 10.6, 7.9 Hz), 6.34 (1H, dd, J = 7.8, 2.1 Hz), 6.07 (1H, s), 4.66-4.57 (1H, m), 3.53-3.45 (1H, m), 3.20 (1H, brs), 3.09 (1H, d, J = 13.4 Hz), 3.05 (1H, d, J = 13.4 Hz), 3.00-2.84 (1H, m), 2.52-2.43 (1H, m), 2.43-2.34 (1H, m), 2.38 (3H, s), 2.32 (3H, s), 2.01-1.66 (2H, m); ESI-MS m/z 528, 530 (MH+). |

| Example | Structural Formula | Physical Value |
|---|---|---|
| Production Example 29 | 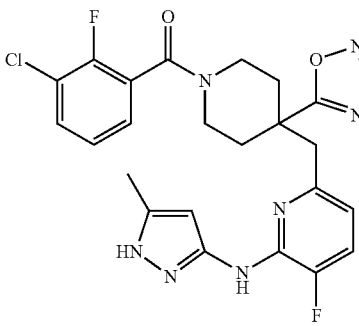 | $^1$H-NMR (CDCl$_3$) δ: 7.45 (1H, ddd, J = 8.3, 6.7, 1.3 Hz), 7.34-7.16 (2H, m), 7.14 (1H, t, J = 7.8 Hz), 7.11 (1H, dd, J = 10.7, 7.8 Hz), 6.34-6.20 (1H, m), 6.11 (1H, s), 4.66-4.50 (1H, m), 3.58-3.40 (1H, m), 3.20-3.02 (1H, m), 3.10 (2H, s), 3.01-2.88 (1H, m), 2.58-2.45 (1H, m), 2.43-2.30 (1H, m), 2.32 (3H, s), 2.26 (3H, s), 2.03-1.65 (2H, brm); ESI-MS m/z 528, 530 (MH+). |

Reference Example 1

Evaluation of Aurora A and Aurora B Inhibitory Effect

The inhibitory activities of a test compound against Aurora A and Aurora B were measured according to the following method. Note that an Aurora A selective inhibitor, MLN8237, presently under clinical development was used as a control compound.

1) Purification of Aurora A Protein

Complementary DNA of human Aurora A was fused with a histidine tag at the amino terminal, inserted into an expression vector and highly expressed in *Escherichia coli* BL21-CodonPlus (DE3)-RIL strain. After *Escherichia coli* was recovered and lysed, human Aurora A protein fused with a histidine tag was allowed to bind to a nickel chelate column and eluted by imidazole from the column. An active fraction was desalted by a desalting column to obtain purified enzyme.

2) Measurement of Aurora A Inhibitory Activity

An inhibitory activity of the above compound in-vitro against Aurora A kinase activity was measured with reference to a method described in JP-A-2008-81492. In measuring inhibitory activity of the compound, first, the test compound was serially diluted by dimethylsulfoxide (DMSO). Then, to a reaction buffer [50 mM Tris-hydrochloric acid buffer (pH 7.4), 15 mM magnesium acetate, 0.2 mM ethylenediamine-N,N,N',N'-tetraacetic acids (EDTA)], purified human Aurora A protein, FL-Peptide 21 (Caliper Life Sciences, Inc., a final concentration: 100 nM), ATP (a final concentration: 5 μM) and the DMSO solution (a final concentration of DMSO: 5%) of the test compound were added. The mixture was incubated at 25° C. for 50 minutes to perform a kinase reaction. To the mixture, IMAP (registered trade mark) Progressive Binding Reagent diluted 500× with IMAP (registered trade mark) Progressive Binding Buffer A (manufactured by Molecular Devices) was added to terminate the kinase reaction. After the mixture was allowed to stand still in a dark place at room temperature for 120 minutes, measurement by PHERAstar (manufactured by BMG LABTECH, excitation wavelength: 485 nm, detection wavelength: 520 nm) was performed. Based on the obtained fluorescence polarization degree, the amount of phosphorylation reaction was obtained. The concentration of the compound at which 50% of the phosphorylation reaction was suppressed was defined as IC$_{50}$ value (nM). The results are shown in Table 17.

3) Measurement of Aurora B Kinase Activity

The method for measuring the in-vitro inhibitory activity of a test compound against Aurora B kinase activity was substantially the same as in the case of Aurora A. A purified recombinant human Aurora B protein was purchased from Carna Biosciences, Inc. The composition of a reaction buffer was 20 mM HEPES (pH 7.4), 2 mM DTT, 0.01% Tween-20, magnesium chloride (final concentration: 1 mM) and ATP (final concentration: 40 μM), and incubation time was set to 60 minutes. The concentration of the compound at which 50% of the phosphorylation reaction was suppressed was defined as IC$_{50}$ value (nM). The results are shown in Table 17.

TABLE 17

| Number of Production Example | Aurora A IC$_{50}$(nM) | Aurora B IC$_{50}$(nM) | Number of Production Example | Aurora A IC$_{50}$(nM) | Aurora B IC$_{50}$(nM) |
|---|---|---|---|---|---|
| 1 | 0.4 | 140 | 19 | 1 | 880 |
| 2 | 0.5 | 340 | 22 | 0.7 | 380 |
| 11 | 0.6 | 930 | 24 | 0.5 | 190 |
| 12 | 0.4 | 260 | 28 | 0.7 | 450 |
| 13 | 0.4 | 180 | 29 | 0.8 | 390 |
| 14 | 0.9 | 460 | MLN8237 | 0.6 | 90 |
| 17 | 0.9 | 900 | | | |

As a result, the compound of the invention exhibited high inhibitory activity against Aurora A and low inhibitory activity against Aurora B, compared to a control compound, MLN8237. It was demonstrated that the compound of the invention has selectivity for Aurora A.

Reference Example 2

Evaluation of Cell-Proliferation Suppression Effect

Human-derived gastric cancer cell strain SNU-16 cells were routinely subcultured in RPMI-1640 medium containing 10% fetal bovine serum (FBS) so as not to exceed a cell density of 80%. To initiate a test for cell proliferation suppression activity, cells were suspended in the above medium and seeded in the wells of a 96 well flat-bottom plate (black plate with a transparent bottom surface) such that the number of cells per well became 2,500 or 3,000 and thereafter, cultured in an incubator containing 5% carbon dioxide gas at 37° C. for one day. The next day, the compound of the invention and a reference compound were separately dissolved in DMSO. The test compound was serially diluted with DMSO up to 200 times of a final concentration. The DMSO solution of the test compound was diluted with the medium used in culturing, added to each of the wells of a cell culture plate such that a final concentration of DMSO reached 0.5%, and cultured in an incubator containing 5% carbon dioxide gas at 37° C. for 72 hours. The number of cells was counted at the time the test compound was added and at the completion of culturing of the cells for 72 hours, by use of CellTiter-Glo Luminescent Cell Viability Assay kit (manufactured by Promega KK.) according to the protocol recommended by Promega KK. A reagent contained in the kit was added to each plate, mixed and allowed to stand still at room temperature for 10 minutes. After completion of the reaction, luminescent signal was measured by use of a microplate reader.

According to the following expression, a cell proliferation inhibition rate was computationally obtained and the concentration ($GI_{50}$ (nM)) of the test compound inhibiting 50% of cell proliferation was obtained. The results are shown in Table 18.

Cell proliferation inhibition rate (%)=$(C-T)/(C-C0)\times 100$

T: Luminescent signal of a well containing the test compound

C: Luminescent signal of a well containing no test compound

C0: Luminescent signal of a well measured before the compound was added

TABLE 18

| Number of Production Example | $GI_{50}$(nM) |
|---|---|
| 1 | 120 |
| 13 | 60 |
| 22 | 970 |

As a result, it was suggested that the compound of the invention has a cell proliferation inhibitory effect and useful as an antitumor agent.

Reference Example 3

Evaluation of Oral Absorption Property

A test compound was suspended or dissolved in 0.5% HPMC and orally administered to BALE/cA mice. At the time points of 0.5, 1, 2, 4 and 6 hours after oral administration, blood was sampled from the back of the eye to obtain blood plasma. The concentration of the compound in the obtained blood plasma was measured by LCMS and evaluated for oral absorption property.

As a result, it was found that the compounds (the compounds of the invention) of Production Examples 1, 11, 12, 13 and 22 were present in sufficient concentrations in the blood plasma after oral administration and had a satisfactory oral absorption property.

Example 1

Study on Schedule of Administration in Combination with Paclitaxel

Cells ($1\times 10^7$) of human-derived uterus cancer cell strain HeLa-luc (manufactured by PerkinElmer Co., Ltd.) having a luciferase gene introduced therein were subcutaneously grafted to the right abdomens of nude rats. At the time the volume of a tumor developed from grafted cells reached about 200 mm³, the rats were divided into groups each consisting of 5 rats according to stratified randomization such that each group had almost the same tumor volume. To the rats of Group 1, paclitaxel (10 mg/kg) alone was intravenously administered on day 1. To Group 2 and 3, paclitaxel was administered and, on the next day, Compound 1 (30 mg/kg) was orally administered twice per day for one day or 4 days (sequential administration, see FIG. 1 (A), Sequential treatment). To the rats of Group 4 and 5, paclitaxel was administered and, on the same day, Compound 1 (30 mg/kg) was orally administered twice per day for 2 days or 4 days (concurrent administration, see FIG. 1 (B), Concurrent treatment). Compound 1 was suspended or dissolved in 0.5% (w/v) hydroxypropyl methyl cellulose (HPMC). Paclitaxel was dissolved in Cremophor EL and anhydrous ethanol, diluted with physiological saline so as to obtain a predetermined concentration and put in use.

The presence or absence of a therapeutic effect was determined by measuring the major axis and minor axis of a tumor with time and obtaining a tumor volume (TV), relative tumor volume (RTV) and T/C (%) value (average relative tumor volume ratio of the treatment group to the control group) on day 10 after initiation of administration according to the following expressions.

Tumor volume (TV)={(major axis)$\times$(minor axis)$^2$}/2

Relative tumor volume ($RTV_n$) on measurement day $(n)=TV_n/TV_1$ $T/C(\%)=\{$(average $RTV_n$ of treatment group)/(average $RTV_n$ of control group)$\}\times 100$ $TV_1$ represents tumor volume at the administration initiation time Furthermore, an individual in which a tumor disappeared was specified as CR (complete remission/complete response) and the number of cases was obtained.

The results are shown in FIG. 1. In Group 1 and 2, no CR cases were observed. In Group 3, the number of CR cases was 2. In Group 4, the number of CR cases was one; whereas in Group 5, the number of CR cases was 4. Furthermore, in Group 3 and 5, no serious toxicity such as death was observed and side effect was allowable.

As is apparent from these, in the sequential administration, CR cases were observed in an administration period of Compound 1 of 2 or more days. Furthermore, in concurrent administration, the number of CR cases was larger in an administration period of Compound 1 of 4 days than 2 days.

Example 2

Study on Schedule of Administration in Combination with Taxane Antitumor Agent (1) Study on Schedule of Administration in Combination with Paclitaxel The study was performed according to the method in Example 1. Cells ($1\times 10^7$) of human-derived lung cancer cell strain NCI-H460 (H460) were subcutaneously grafted to right abdomens of nude mice. At the time the volume of a tumor developed from grafted cells reached 80 to 120 mm³, the mice were divided into 5 groups each consisting of 10 mice according to stratified randomization such that each group had almost the same tumor volume (day 1). Group 1 was defined as a control group, Group 2 and 3 were defined as a paclitaxel single administration group and Compound 1 single administration group, respectively. Group 4 and 5 were defined as an administration group in combination with paclitaxel and Compound 1. Paclitaxel was intravenously administered in a dose of 60 mg/kg twice, i.e., day 1 and day 8 (Group 2, 4 and 5). In Group 3 and 5, Compound 1 was orally administered twice per day in a dose of 60 mg/kg, for 4 days from the next day of paclitaxel administration and for 4 days from day 9 of paclitaxel administration. In Group 4, Compound 1 was orally administered twice per day in a dose of 60 mg/kg from the next day of paclitaxel administration for 2 days and from day 9 for 2 days. In Group 3, 4 and 5, the dose per day of Compound 1 was 120 mg/kg/day. Compound 1 was suspended or dissolved in 0.5% (w/v) hydroxypropyl methyl cellulose (HPMC). Paclitaxel was dissolved in Cremophor EL and anhydrous ethanol, diluted with physiological saline so as to obtain a predetermined concentration and administered. To the mice of the control group (Group 1) and single administration groups (Group 2 and 3), the corresponding ones of the solvents as used in preparing Compound 1 or paclitaxel administration liquid, were administered. In this manner, the solvent conditions of individual groups were set to be equal.

The presence or absence of a therapeutic effect was determined by measuring the major axis and minor axis of a tumor with time and obtaining a tumor volume (TV), according to the following expression. The results are shown in FIG. 2 (A).

$$\text{Tumor volume (TV)} = \{(\text{major axis}) \times (\text{minor axis})^2\}/2$$

Furthermore, the body weights of mice were measured with time and a body weight change rate (BWC) was computationally obtained according to the following expression.

$$\text{BWC (\%)} \times \{(\text{body weight at each measurement day}) - (\text{body weight at the administration initiation time})\}/\text{body weight at the administration initiation time} \times 100$$

Note that, in FIG. 2 (A), Group 1 is represented by Control, Group 2 by Paclitaxel alone, Group 3 by Compound 1 alone, Group 4 by Combo (2 days), and group 5 by Combo (4 days). Note that no significant toxicity such as death was observed in Group 4 and 5 and side effect was allowable.

(2) Study on Schedule of Administration in Combination with Docetaxel

The study was performed according to the method in Example 1, except that docetaxel was used in place of paclitaxel. Furthermore, administration of Compound 1 was initiated from the administration day of docetaxel. Group 1 was defined as a control group. Docetaxel was dissolved in anhydrous ethanol and Tween 80 and thereafter diluted with 5% glucose injection liquid and intravenously administered in a dose of 30 mg/kg twice, i.e., on day 1 and day 8 (Group 2 and 4). In Group 3 and 4, Compound 1 was orally administered twice per day in a dose of 60 mg/kg, from the administration day of docetaxel for 4 days and from day 8 of docetaxel administration for 4 days.

The presence or absence of a therapeutic effect was determined by obtaining tumor volume (TV) according to the same expression as in the above (1). The results are shown in FIG. 2 (B). Note that no significant toxicity such as death was observed in Group 4 and side effect was allowable.

In Group 3 and 4, the dose of Compound 1 per day was 120 mg/kg/day. Note that, in FIG. 2 (B), Group 1 is represented by Control, Group 2 by Docetaxel alone, Group 3 by Compound 1 alone and Group 4 by Combo (4 days).

In FIG. 2 (A), the tumor volume of Group 5 is smaller than that of Group 4. As a result of a significance test on tumor volume, p values of day 8, day 15 and day 18 are less than 0.05, meaning that there is a significant difference in tumor volume. Furthermore, in FIG. 2 (B), an antitumor effect is exerted by administration of Compound 1 for 4 days in the case of docetaxel similarly to paclitaxel.

As is apparent from these, in administration with 7 days as one cycle, a stronger antitumor enhancing effect of Compound 1 was observed in an administration period of 4 days than in that of 2 days.

Example 3

(1) Study on Schedule of Administration in Combination with Paclitaxel

In this test, the following evaluation was performed by using a hydrochloride salt form of Compound 1. The hydrochloride salt form of Compound 1 was synthesized from Compound 1 by a method routinely used.

Cells ($1 \times 10^7$) of human-derived ovarian cancer cell strain A2780 were subcutaneously grafted to right abdomens of nude mice. At the time the volume of a tumor developed from grafted cells reached 150 to 300 mm$^3$, the mice were divided into 4 groups each consisting of 5 mice according to stratified randomization such that each group had almost the same tumor volume (day 1). Group 1 was defined as a control group, Group 2 was defined as a paclitaxel single administration group and Group 3 and 4 were defined as an administration group in combination with paclitaxel and the hydrochloride salt form of Compound 1. Paclitaxel was intravenously administered in a dose of 60 mg/kg on day 1 (Group 2, 3 and 4). In Group 3, the hydrochloride salt form of Compound 1 was orally administered twice per day in a dose of 60 mg/kg, from the same day as the paclitaxel administration day for 4 days. In FIG. 3 (A), Group 3 is represented by Paclitaxel/Compound 1 HCl salt, 60 mg/kg, day 1-4 (bid). In Group 4, the hydrochloride salt form of Compound 1 was orally administered twice per day in a dose of 60 mg/kg from the same day as the paclitaxel administration day for 7 days. In FIG. 3 (A), Group 4 is represented by Paclitaxel/Compound 1 HCl salt, 60 mg/kg, day 1-7 (bid). The hydrochloride salt form of Compound 1 was suspended in 0.5% (w/v) hydroxypropyl methyl cellulose (HPMC) and then dissolved by adding an aqueous sodium hydroxide solution in a volume of 2 equivalents relative to the hydrochloride salt form of Compound 1. Paclitaxel was dissolved in Cremophor EL and anhydrous ethanol, diluted with physiological saline so as to obtain a predetermined concentration and administered. To mice of the control group (Group 1) and the single administration group (Group 2), the corresponding ones of the solvents as used in preparing the hydrochloride salt form of Compound 1 or paclitaxel administration liquid, were administered. In this manner, the solvent conditions of individual groups were set to be equal.

The presence or absence of a therapeutic effect was determined by measuring the major axis and minor axis of a tumor with time, obtaining a tumor volume (TV), relative tumor volume (RTV) and T/C (%) value (average relative tumor volume ratios of the treatment group to the control group) on day 10 and day 21 after initiation of administration, according to the following expressions and subjecting values to the significance test. The results are shown in FIG. 3 (A). Note that in Group 3 and 4, no significant toxicity such as death was observed and side effect was allowable.

$$\text{Tumor volume (TV)} = \{(\text{major axis}) \times (\text{minor axis})^2\}/2$$

$$\text{Relative tumor volume (RTV}_n\text{) on measurement day } (n) = TV_n/TV_1$$

$$T/C(\%) = \{(\text{average RTV}_n \text{ of treatment group})/(\text{average RTV}_n \text{ of control group})\} \times 100$$

TV₁ represents tumor volume at the administration initiation time

Furthermore, the body weights of mice were measured with time and body weight change rate (BWC) was computationally obtained according to the following expression.

BWC (%)={(body weight at each measurement day)−(body weight at the administration initiation time)}/body weight at the administration initiation time×100

(2) Study on Schedule of Administration in Combination with Docetaxel

Group 1 is defined as a control group, Group 2 and 3 as a hydrochloride salt form of Compound 1 single administration group and a docetaxel single administration group, respectively, and Group 4 to 6 as administration groups in combination with docetaxel and the hydrochloride salt form of Compound 1. Docetaxel was intravenously administered in a dose of 20 mg/kg on day 1. The hydrochloride salt form of Compound 1 was orally administered twice per day on the same day as the paclitaxel administration day in a dose of 60 mg/kg. In Group 4 to 6, the hydrochloride salt form of Compound 1 was orally administered twice a day from the same day as the docetaxel administration day for 4 days, 7 days and 12 days, respectively. The hydrochloride salt form of Compound 1 was suspended in 0.5% (w/v) hydroxypropyl methyl cellulose (HPMC) and then dissolved by adding an aqueous sodium hydroxide solution in a volume of 2 equivalents relative to the hydrochloride salt form of Compound 1. Docetaxel was dissolved in anhydrous ethanol and Tween 80 and diluted with physiological saline so as to obtain a predetermined concentration and administered. To mice of the control group (Group 1) and single administration groups (Group 2 and 3), the corresponding ones of the solvents as used in preparing the hydrochloride salt form of Compound 1 or docetaxel administration liquid, were administered. In this manner, the solvent conditions of individual groups were set to be equal. The presence or absence of a therapeutic effect was determined by measuring the major axis and minor axis of a tumor with time, obtaining a tumor volume (TV), and relative tumor volume (RTV) and T/C (%) values (average relative tumor volume ratio of the treatment group to the control group) on day 12 and day 22 after initiation of administration according to the same expression as the above (1), and subjecting the values to significance test. The results are shown in FIG. 3 (B). Note that in Group 4 to 6, no significant toxicity such as death was observed and side effect was allowable. Furthermore, in FIG. 3 (B), Group 4 is represented by Combo (day 1-4), Group 5 by Combo (day 1-7) and Group 6 by Combo (day 1-12).

Significance tests for tumor volumes of Group 3 and 4 were performed and the results are shown in FIG. 3 (A). As a result, p values of day 7 and day 22 were 0.31 and 0.88, respectively. There was no significant difference in tumor volume.

In FIG. 3 (B), the tumor volumes of Group 4, 5 and 6 significantly decreased compared to single administration groups (Group 2 and 3).

As is apparent from these, when paclitaxel was used, the same antitumor enhancing effect was obtained in the cases of administering the hydrochloride salt form of Compound 1 for 4 days and 7 days. When docetaxel was used, a strong antitumor enhancing effect was obtained if the hydrochloride salt form of Compound 1 is administered for 4 days or more.

What is claimed is:

1. A method for enhancing an antitumor effect of a microtubule-targeting drug, the method comprising administering a piperidine compound of formula (I) or a salt thereof once or more per day for 4 days or more, and the microtubule-targeting drug once per 7 days or more as one cycle, wherein the microtubule-targeting drug is a taxane antitumor agent:

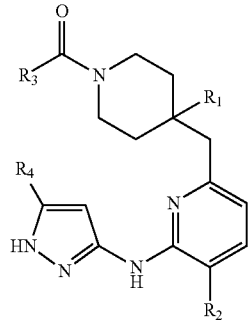

and wherein $R_1$ represents a carboxyl group, $-C(=O)NR_5R_6$, or an oxadiazolyl group which is optionally substituted with a $C_1$-$C_6$ alkyl group or a trifluoromethyl group;
$R_2$ represents a halogen atom or a $C_1$-$C_6$ alkoxy group;
$R_3$ represents a phenyl group which is optionally substituted with 1 to 3 groups, which are the same or different, selected from the group consisting of a halogen atom, a $C_1$-$C_6$ alkyl group, a $C_1$-$C_6$ alkoxy group and a trifluoromethyl group, as a substituent;
$R_4$ represents a hydrogen atom or a $C_1$-$C_6$ alkyl group; and
$R_5$ and $R_6$, which are the same or different, each independently represent a hydrogen atom, a $C_1$-$C_6$ alkyl group or a $C_3$-$C_6$ cycloalkyl group, or $R_5$ and $R_6$, together with a nitrogen atom to which they are attached, optionally form a 3 to 6-membered saturated heterocyclic group comprising nitrogen.

2. The method according to claim 1, wherein
the microtubule-targeting drug is administered on day 1 in 7 days as one cycle, and
administration of the piperidine compound or a salt thereof is initiated on day 1 or day 2, wherein a period of consecutive daily administration is performed for 4 or 5 days.

3. The method according to claim 1, wherein
the microtubule-targeting drug is administered on day 1 in 21 days as one cycle, and
administration of the piperidine compound or a salt thereof is initiated on day 1 or day 2, wherein a period of consecutive daily administration is performed for 4 to 12 days.

4. The method according to claim 1, wherein the piperidine compound or a salt thereof is 1-(2,3-dichlorobenzoyl)-4-(5-fluoro-6-(5-methyl-1H-pyrazol-3-ylamino)pyridin-2-yl)methyl)piperidine-4-carboxylic acid or a salt thereof.

5. The method according to claim 1, wherein the taxane antitumor agent is paclitaxel, docetaxel, cabazitaxel, albumin-binding paclitaxel, albumin-binding docetaxel, docosahexaenoic acid binding paclitaxel, polyglutamated paclitaxel or peptide-binding paclitaxel.

6. A method for treating a tumor, comprising
administering a piperidine compound of formula (I) or a salt thereof once or more per day for 4 days or more in combination with a microtubule-targeting drug administered-once per 7 days or more as one cycle, wherein the microtubule-targeting drug is a taxane antitumor agent and the piperidine compound or a salt thereof is administered once or more per day for 4 days or more:

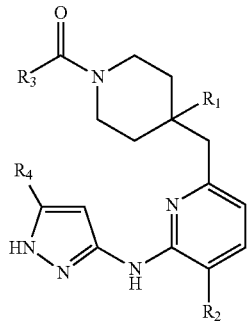

and wherein $R_1$ represents a carboxyl group, —C(=O)$NR_5R_6$, or an oxadiazolyl group which is optionally substituted with a $C_1$-$C_6$ alkyl group or a trifluoromethyl group;

$R_2$ represents a halogen atom or a $C_1$-$C_6$ alkoxy group;

$R_3$ represents a phenyl group which is optionally substituted with 1 to 3 groups, which are the same or different, selected from the group consisting of a halogen atom, a $C_1$-$C_6$ alkyl group, a $C_1$-$C_6$ alkoxy group and a trifluoromethyl group, as a substituent;

$R_4$ represents a hydrogen atom or a $C_1$-$C_6$ alkyl group; and $R_5$ and $R_6$, which are the same or different, each independently represent a hydrogen atom, a $C_1$-$C_6$ alkyl group or a $C_3$-$C_6$ cycloalkyl group; or $R_5$ and $R_6$, together with a nitrogen atom to which they are attached, optionally form a 3 to 6-membered saturated heterocyclic group comprising nitrogen.

7. The method according to claim 6, wherein
the microtubule-targeting drug is administered on day 1 in 7 days as one cycle, and
administration of the piperidine compound or a salt thereof is initiated on day 1 or day 2, wherein a period of consecutive daily administration is performed for 4 or 5 days.

8. The method according to claim 6, wherein
the microtubule-targeting drug is administered on day 1 in 21 days as one cycle, and
administration of the piperidine compound or a salt thereof is initiated on day 1 or day 2, wherein a period of consecutive daily administration is performed for 4 to 12 days.

9. The method according to claim 6, wherein the piperidine compound or a salt thereof is 1-(2,3-dichlorobenzoyl)-4-(5-fluoro-6-(5-methyl-1H-pyrazol-3-ylamino)pyridin-2-yl)methyl)piperidine-4-carboxylic acid or a salt thereof.

10. The method according to claim 6, wherein the taxane antitumor agent is paclitaxel, docetaxel, cabazitaxel, albumin-binding paclitaxel, albumin-binding docetaxel, docosahexaenoic acid binding paclitaxel, polyglutamated paclitaxel or peptide-binding paclitaxel.

11. The method according to claim 4, wherein the taxane antitumor agent is paclitaxel, docetaxel, cabazitaxel, albumin-binding paclitaxel, albumin-binding docetaxel, docosahexaenoic acid binding paclitaxel, polyglutamated paclitaxel or peptide-binding paclitaxel.

12. The method according to claim 9, wherein the taxane antitumor agent is paclitaxel, docetaxel, cabazitaxel, albumin-binding paclitaxel, albumin-binding docetaxel, docosahexaenoic acid binding paclitaxel, polyglutamated paclitaxel or peptide-binding paclitaxel.

\* \* \* \* \*